US006242477B1

(12) United States Patent
Okamoto et al.

(10) Patent No.: US 6,242,477 B1
(45) Date of Patent: Jun. 5, 2001

(54) PHARMACEUTICAL COMPOSITIONS CONTAINING PYRYLIUM COMPOUNDS, PYRYLIUM SALTS AND PROCESS FOR MANUFACTURING A MEDICAMENT CONTAINING THE AFORESAID COMPOUNDS

(75) Inventors: Tadashi Okamoto, Yokohama; Nobuko Yamamoto, Isehara; Masahiro Kawaguchi, Atsugi, all of (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/343,941

(22) Filed: Jun. 30, 1999

Related U.S. Application Data

(62) Division of application No. 08/878,125, filed on Jun. 18, 1997, now Pat. No. 6,124,342, which is a continuation of application No. 08/363,955, filed on Dec. 27, 1994, now abandoned.

(30) Foreign Application Priority Data

Dec. 27, 1993 (JP) .................................................. 5-330561
Oct. 17, 1994 (JP) .................................................. 6-250848

(51) Int. Cl.$^7$ ................................................ A61K 31/35
(52) U.S. Cl. ........................ 514/432; 514/451; 514/460; 607/88; 607/94
(58) Field of Search .................................. 514/432, 451, 514/460; 607/88, 94

(56) References Cited

U.S. PATENT DOCUMENTS

| | | | |
|---|---|---|---|
| 3,786,369 | 1/1974 | Drexhage et al. | 331/94.5 |
| 4,341,894 | 7/1982 | Regan et al. | 544/333 |
| 4,555,396 | 11/1985 | Frank et al. | 424/3 |
| 4,774,250 | 9/1988 | Chen et al. | 514/336 |
| 4,840,784 | 6/1989 | Frank et al. | 424/3 |
| 4,992,257 | 2/1991 | Bonnett et al. | 424/9 |
| 5,047,419 | 9/1991 | Detty et al. | 514/432 |
| 5,162,519 | 11/1992 | Bonnett et al. | 540/145 |
| 5,229,297 | 7/1993 | Schnipelsky et al. | 436/94 |
| 5,278,043 | 1/1994 | Bannwarth et al. | 536/23.1 |
| 5,624,798 | 4/1997 | Yamamoto et al. | 435/6 |
| 5,670,315 | 9/1997 | Yamamoto et al. | 435/6 |
| 5,705,346 | 1/1998 | Okamoto et al. | 435/6 |

FOREIGN PATENT DOCUMENTS

| | | |
|---|---|---|
| 0 229 943 A3 | 7/1987 | (EP) . |
| 0 232 967 A3 | 8/1987 | (EP) . |
| 0 294 921 A2 | 12/1988 | (EP) . |
| 0 315 491 A2 | 5/1989 | (EP) . |
| 0 367 449 A1 | 5/1990 | (EP) . |
| 0 439 036 A2 | 7/1991 | (EP) . |
| 0 487 218 A1 | 5/1992 | (EP) . |
| 0 512 334 A2 | 11/1992 | (EP) . |
| 0 603 783 A1 | 6/1994 | (EP) . |
| 0 643 140 A1 | 3/1995 | (EP) . |
| 59-133460 | 7/1984 | (JP) . |
| 64-52715 | 2/1989 | (JP) . |
| 1-153683 | 6/1989 | (JP) . |
| 1-275528 | 11/1989 | (JP) . |
| 2-75958 | 3/1990 | (JP) . |
| 2-295496 | 12/1990 | (JP) . |
| 86/03227 | 6/1986 | (WO) . |
| 86/06374 | 11/1986 | (WO) . |
| 89/10415 | 11/1989 | (WO) . |

OTHER PUBLICATIONS

Brun, et al., "Dynamics of Electron Transfer between Intercalated Polycyclic Molecules: Effect of Interspersed Bases", J. Am. Chem. Soc., vol. 114, pp. 3656–3660, 1992.

Cardullo, et al., "Detection of nucleic acid hybridization by nonradiative fluorescence resonance energy transfer", Proc. Natl. Acad. Sci., vol. 85, pp 8790–8794, Dec. 1988.

Rahman, et al., "Complexes involving quercetin, DNA and Cu(II)", Carcinogenesis, vol. 11, No. 11, pp. 2001–2003, 1990.

Balaban, et al., "Charge–Transfer Spectra of Pyrylium Iodides", Tetrahedron, vol. 20, pp. 119–130, 1964.

Morrison, et al., "Solution–Phase Detection of Polynucleotides Using Interacting Fluorescent Labels and Competitive Hybridization", Anal. Biochem., vol. 183, pp. 231–244, 1989.

Basting, et al., "New Laser Dyes", Appl. Phys., vol. 3, pp. 81–88, 1974.

Latt, et al., "New Fluorochromes, Compatible With High Wavelength Excitation, for Flow Cytometric Analysis of Cellular Nucleic Acids", Cytometry, vol. 5, pp. 339–347, 1984.

Murphy, et al., "Long–Range Photoinduced Electron Transfer Through a DNA Helix", Science, vol. 262, pp. 1025–1029, Nov. 12, 1993.

Smits, et al., "Relationship between Solvation as Expressed by the Walden Product and Cation Exchange Selectivity in Water–Dimethylsulfoxide", Anal. Chem., vol. 45, No. 2, pp. 339–342, 1973.

(List continued on next page.)

*Primary Examiner*—Frederick Krass
(74) *Attorney, Agent, or Firm*—Fitzpatrick, Cella, Harper & Scinto

(57) ABSTRACT

The present invention provides pharmaceutical compositions containing a pyrylium compound, a thiopyrylium compound, a selenopyrylium compound or a telluropyrylium compound or a salt of any of the aforesaid compounds as active ingredient. The compounds are selectively absorbed by cancer cells or similar growths in the human or animal body and can be used to bring about distruction of the unwanted growth an irradiation with light of wavelength 600 nm to 1000 nm. The invention also provides a method for the treatment of the human or animal body which comprises administering the compound to a human or animal and irradiating a locus in said animal where the compound is absorbed in order to kill cells at that locus. It further comprises the use of the aforesaid compound for the making of a medicament for use in the treatment of cancer in humans and animals.

7 Claims, No Drawings

OTHER PUBLICATIONS

Fromherz, et al., "Photoinduced Electron transfer in DNA Matrix from Intercalated Ethidium to Condensed Methylviologen", J. Am. Chem. Soc., vol. 108, pp. 5361–5362, 1986.

Ulicky, et al., "Comprehensive Dictionary of Physical Chemistry", p. 103, 1992.

Detty, et al., "Chalcogenapyrylium Dyes as Photochemotheraupeutic agents. 2. Tumor Uptake, Mitochondrial Targeting, and Singlet–Oxygen–Induced Inhibition of Cytochrome c Oxidase", J. Med. Chem, vol. 33, pp. 1108–1116, 1990.

Balaban, et al., "Regioselective Deuteriation Kinetics of 2–,4–and 6–Methyl Groups in $D_2O$ Solutions of Pyrylium and N–Methylpyridinium Perchlorates Possessing also 3–Methyl ro 3–Phenyl Groups", J. Labelled Cmpds. and Radiopharm., vol. 19, No. 6, pp. 783–793, 1982.

Detty, "Rational design of properties in chalgogenapyrylium dyes.", New Directions in Photodynamic Therapy, vol. 847, pp. 68–73, 1987.

Yamamoto, et al., "Novel intercalators of pyrylium dye into double–stranded DNA", Nucleic Acids Sym., Series No. 29, pp. 83–84, 1993.

Sanford, et al., "The Growth in Vitro of Single Isolated Tissue Cells", Nat'l. Cancer Inst., vol. 9, No. 3, pp. 229–246, Dec. 1948.

Haucke, et al., "Absorption and Fluorescence of Pyrylium Salts", Phys. Chem. vol. 96, No. 7, pp. 880–886, 1992.

Roberts, et al., "In Vitro Characterization of Monoaspartyl Chlorin $e_6$ and Diaspartyl Chlorin $e_6$ for Photodynamic Therapy", Journal of the Nat'l Cancer Inst., vol. 80, No. 5, pp. 330–336, May 4, 1988.

Manyak, et al., "Photodynamic Therapy", vol. 6, No. 2, pp. 380–391, Feb. 1988.

Wizinger, et al., Helvetica Chimica Acta., vol. 39, No. 24, pp. 217–222, 1956.

Detty, et al., "Chalcogenapyrylium Dyes as Dual–Action Sensitizers for Photodynamic Therapy", Oncology Research, vol. 4, No. 8/9, pp 367–373, 1992.

Foerst, "New Methods of Preparative Organic Chemistry", Acad. Press, one page, 1964.

Shimidzu, et al., "Syntheses of oligonucleotide derivatives iwth P(V) porphyrin and their properties", 19th Symp. on Nuc. Acids. Chem, pp. 97–98, 1992.

Wizinger, et al., Helv. Chim. Acta, vol. 39, No. 2, Fas. I, pp. 5–15, 1956.

Newer Methods of Prep. Org. Chem., vol. II, Acad. Press pp. ix–xiv, 1963.

PHARMACEUTICAL COMPOSITIONS CONTAINING PYRYLIUM COMPOUNDS, PYRYLIUM SALTS AND PROCESS FOR MANUFACTURING A MEDICAMENT CONTAINING THE AFORESAID COMPOUNDS

This application is a division of application Ser. No. 08/878,125, filed Jun. 18, 1997, now U.S. Pat. No. 6,124,342; which is a continuation of application Ser. No. 08/363,955, filed Dec. 27, 1994, now abandoned.

BACKGROUND OF THE INVENTION

1. Field of the invention

The present invention relates to a pharmaceutical composition containing a pyrylium compound, thiopyrylium compound, selenopyrylium compound or telluropyrylium compound (hereinafter referred to as "a pyrylium compound") or a salt of any of the aforesaid compounds as active ingredient. It also provides a method for the treatment of the human and animal body which comprises administering the compound to a human or animal and irradiating a locus in said animal where the compound is absorbed in order to kill cells at that locus. It further comprises the use of the aforesaid compound for making a medicament for use in the treatment of cancer in humans and animals.

2. Related Art

In the pharmaceutical field, one of the most important problems is to find medicaments for use in the treatment of cancer. One approach to the treatment of cancer is to use photochemistry. Extensive research has been carried out into the photochemical treatment of cancer, and it has been put into clinical use since 1976. There is an extensive journal and patent literature concerning photochemical treatments for cancer, see for example the general remarks of Michael J. Manya (J. Clin. Oncology, vol. 6, 1988, pp. 380–391). In these literature and patent references almost all the medicaments which have been adminstered to enable photochemical treatment to be carried out contain a porphyrin compound, particularly hematoporphyrin derivatives (HPD) or diamatoporphyrin derivatives (DHE) which have been applied clinically, and a medicament called PHOTOFRIN which contains DHE is expected to be marketed shortly by LEDERLE JAPAN Co. Ltd.

The way in which photochemical treatment is carried out using a medicament containing a porphyrin-type compound will now be explained. When this medicament is given to a patient suffering from cancer, then almost all the active material is metabolised by normal cells in a few days (48 to 72 hours). However, medicament absorbed by cancer cells is not metabolised, and the amount thereof that builds up in the cell is from several times to several tens of times that in a normal cell. Then the cancer cells and surrounding tissue is irradiated with light of frequency 600–700 nm, and the cancer cells in which the medicament has built up die preferentially whilst normal cells are generally unaffected by the radiation. Accordingly, it is possible to treat cancer in this way without producing unacceptable side effects. The reason why the medicament remains preferentially in the cancer cells is not clear, but it is believed to be the result of a difference in blood circulation between the cancer cells and normal cells. It is also not clear why cancer cells in which the medicament is present die when subjected to irradiation. However, it is believed that radiant energy absorbed by the medicament brings about transformation of oxygen in the vicinity of the cancer cells into singlet oxygen which has strong cytotoxicity.

The photochemical method of treatment has some problems, one of which is the mismatch of the wavelength at which the porphyrin-type compound absorbs light and the wavelength of the radiation which can be used. For irradiating cells it is desirable to use radiation having a wavelength from 600 nm to near infrared. The first reason is that it is necessary for the radiation to penetrate into the living tissue. For example, in the case of a skin cancer the radiation should penetrate the skin to a depth of several millimetres. Radiation of 600 nm wavelength or less is absorbed or scattered by substances in the living body and does not penetrate to the desired depth. The second reason is that it is necessary to avoid any radiation damage to the hemoglobin in red blood corpuscles. Oxidised hemoglobin has absorption peaks at 540 nm and 577 nm and reduced hemoglobin has an absorption peak at 555 nm. The energy of the radiation used for irradiation treatment is so strong that when a living body is irradiated with light of wavelength 500–600 nm, hemoglobin is damaged. Furthermore, it is undesirable to use for treatment radiation having a wavelength of 1200 nm or above because that radiation brings about heating of the living tissue.

For the above reasons it is apparent it is necessary to use for treatment radiation having a wavelength of 600–1000 nm. However, DHE has a maximum absorption peak at 363 nm and at wavelengths of 600 nm or above, DHE has an absorption of only 2–3% of the peak ($\epsilon$ 630 nm=$3.6 \times 10^3$ l/mol.cm; W. Roberts et al, J. Natl. Cancer Inst., vol. 80, 1988, pp. 330–336). Therefore the absorption of the light used for treatment is inefficient and it is necessary to increase the amount of medicament to be administered or to increase the intensity of the irradiating light. This requires expensive apparatus for the treatment, and give rise to harmful after-effects.

Various investigations have been made with the object of overcoming these problems. For example, Japanese laid open Patent Application JP-A-1-275528 discloses porphyrin-type compounds which have been modified to extend their absorption wavelength and to increase their strength of absorption. The compound exhibiting the strongest absorption has an extinction coefficient $\epsilon$ of $2.24 \times 10^4$ l/mol.cm at 630 nm wavelength. This patent also discloses a further type of compounds whose absorption strength is stronger However, it does not disclose that these compounds exhibit anti-tumour characteristics.

In a paper written by W. Roberts a method is disclosed for synthesising a compound having an absorption peak with an extinction coefficient of $3.8 \times 10^4$ l/mol.cm at 630 nm wavelength. However, in order to improve the efficiency of the treatment, a medicament having an absorption peak at longer wavelengths and having a greater extinction coefficient is desired.

According to Nikkan Kogyo Shimbun on Jun. 7, 1993, further research on MONOASPARTYLCHLORIN by Nippon Sekiyu Kagaku K.K., on PHEOPHORBIDE by Hamari Yakuhin Kogyo K.K., on ZINCFLIN by Asahi Kasei Kogyo K.K. were reported. However, these compounds are still in the research stage, and almost all the investigations now being carried out concern porphyrin-type compounds whose mode of action on cancer cells is as described above.

Titanium dioxide has been investigated as an anti-cancer medicament whose mode of action on cancer cells differs from medicaments based on porphyrin-type compounds. However, in this approach there is a difficulty in transporting the titanium dioxide selectively to the cancer cells and ultraviolet radiation is required for treatment.

SUMMARY OF THE INVENTION

It is therefore an object of the present invention to provide a new medicament which can be used in the photochemical treatment of cancer, or similar growths that occur in the body at one or more definable places.

In one aspect of the present invention there is provided a medicament for the photochemical treatment of a human or animal body, said medicament containing as an effective component a compound represented by the formula

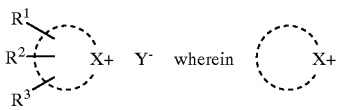

[I]

is a heterocyclic ring, X represents O, S, Se or Te and the heterocyclic ring is a 5 or 6 membered ring, for example a pyrylium ring or a pyrylium-type ring;

a hydrogen atom, a halogen atom, a sulfonate group, an amino group, a styryl group, a nitro group, a hydroxyl group, a carboxyl group, a cyano group, a substituted or unsubstituted lower alkyl group, a substituted or unsubstituted aryl group, a substituted or unsubstituted lower alkyl group, or a substituted or unsubstituted cycloalkyl group;

$R^3$ is —A or —L—A in which L represents —$L^1$—, —$L^2$—$L^3$—or $L^4$—$L^5$—$L^6$— and each of $L^1$ to $L^6$ independently represents —(CH=CH)—, a divalent group derived from the substituted or unsubstituted aryl group, a substituted or unsubstituted lower alkylene group or —CH=$R^4$— ($R^4$ is a ring structure having an oxo group).

An example of a divalent group derived from a substituted or unsubstituted aryl group is a phenylene group to which substituents may be bonded at any of the ortho, meta and para positions. An example of the lower alkylene group is a straight-chain or branched alkylene group having 1 to 4 carbon atoms, and an example of a substituent on the lower alkylene group is a group represented by —L—A. Examples of the ring structure having the oxo group include a heterocyclic ring, aromatic ring and aliphatic ring having at least the oxo group.

Preferable example of —L— include groups represented by Preferable example of include groups represented by the formulae [II], [III], [IV], [V] and [IV];

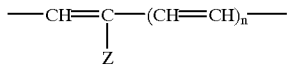

[II]

(wherein z is a hydrogen atom or a substituted or unsubstituted lower alkylene group, and n is 0, 1 or 2). An example of a substituent on the alkyl group represented by Z is a group defined by the above-mentioned —L—A.

[III]

(wherein n is 0, 1 or 2, and Φ f is a substituted or unsubstituted o-, m- or p-phenylene group.)

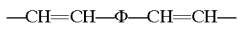

[IV]

(wherein Φ is a substituted or unsubstituted o-, m- or p-phenylene group.)

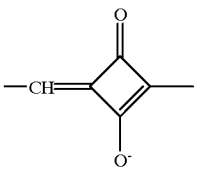

[V]

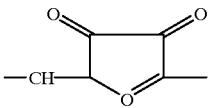

[VI]

A substituent of the phenylene group in the above-mentioned formulae is previously exemplified.

A in $R^3$ of the formula [I] is a substituted or unsubstituted aryl group or —CH=$R^5$— ($R^5$ is a substituted or unsubstituted heterocyclic ring, a substituted or unsubstituted cycloalkyl group, or a substituted or unsubstituted aromatic ring). Examples of the heterocyclic ring represented by $R^5$ include groups derived from rings represented as follows:

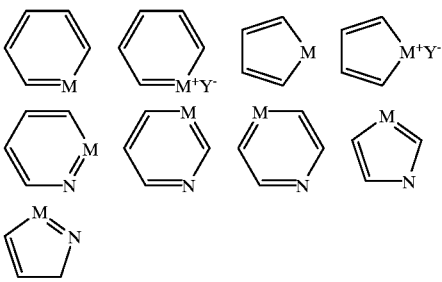

(each of X and N is independently an oxygen atom, sulfur atom or nitrogen atom, and $Y^-$ is an anion), and an example of a substituent on the heterocyclic ring is a substituted or unsubstituted aryl group. The substituted or unsubstituted cycloalkyl group may be saturated or unsaturated, and examples of the substituted or unsubstituted cycloalkyl groups include groups derived from resonance systems such as

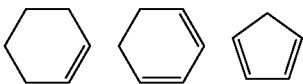

Furthermore, an example of the substituted or unsubstituted aromatic ring is an azulene ring. Examples of substituents on these groups include lower alkyl groups and substituted or unsubstituted aryl groups.

The hydrogen atom bonded to a carbon atom not having $R^1$, $R^2$ and $R^3$ on the pyrylium ring or its similar ring containing X may be substituted by a halogen atom, sulfonate group, amino group, styryl group, nitro group, hydroxyl group, carboxyl group, cyano group, substituted and unsubstituted lower alkyl group, substituted or unsubstituted aryl group, or substituted or unsubstituted lower alkyl group.

$Y^-$ is an anion, and examples of the anion include $BF_4^-$, a perchlorate ion, $HO_3SCH_2COO^-$, halogen ions such as a chlorine ion, bromine ion, iodine ion and fluorine ion, compounds having an anionic function such as aliphatic hydrocarbons and aromatic sulfonates, and complex ions of transition metals such as Zn, Ni, Cu, Pt, Co and Pd.

A group which is further substituted on the various above-mentioned substituents may be a halogen atom, and examples of the halogen atoms include Cl, Br and I. Moreover, the lower alkyl group may be straightchain or branched, and the number of carbon atoms in this lower alkyl group is preferably from 1 to 4. An example of the aryl group is a phenyl group. An example of a substituent on the aryl group or phenylene group is an amino group substituted by a lower alkyl group (a lower alkylamino group). This lower alkylamino group is preferably substituted by a dimethylamino group or dimethylamono group at the para position. An example of the lower aralkyl group is a lower alkyl group substituted by the above-mentioned substituted or unsubstituted aryl group.

Among the compounds represented by the formula [I], preferable are compounds in which the heterocyclic ring containing X is substituted by the two or more substituted or unsubstituted aryl groups. For example, when the heterocyclic ring containg X is a six-membered ring, examples of such compounds include:

(1) a compound in which the 2-position and 4-position of the six-membered ring containg X are substituted by the substituted or unsubstituted aryl groups, and any of the 3-position, 5-position and 6-position is substituted by $R^3$, (2) a compound in which the 3-position and 5-position of the six-membered ring are substituted by the substituted or unsubstituted aryl groups, and any of the 2-position, 4-position and 6-position is substituted by $R^3$, (3) a compound in which the 2-position and 6-position of the six-membered ring are substituted by the substituted or unsubstituted aryl groups, and any of the 3-position, 4-position and 5-position is substituted by $R^3$.

The introduction of the substituted or unsubstituted aryl groups into such positions is preferable to obtain good characteristics as an intercalater to the base pair of the nucleic acid. In addition, more preferable is a compound in which the heterocylic ring containing X is substituted by two or more of the substituted or unsubstituted aryl groups so that these substituted positions may not be adjacent to each other.

Typical examples of the compounds represented by the formula [I] include compounds shown in Table 1 given below. Furthermore, particularly preferable examples are compounds represented by the formula [VII]

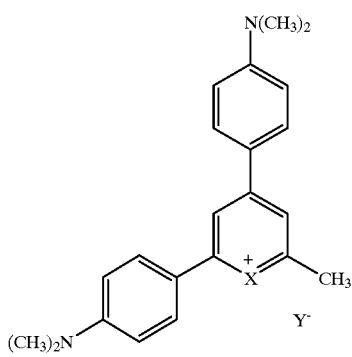

[VII]

(wherein X is O or S, and Y⁻ is an anion), and compounds represented by the formula [VIII]

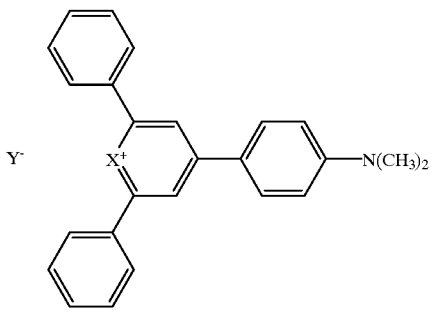

[VIII]

(wherein X is O or S, and Y⁻ is an anion).

As described above, compounds which can be used as active ingredient of a medicament for the photochemical treatment of cancer according to the present invention are salts of pyrylium-type compounds.

Such pyrylium-type compounds have been investigated since the beginning of the twentieth century. Early research was mainly concerned with methods for synthesing these compounds and characterising them as a dye. However, their electron transfer properties have recently attracted attention, and these compounds have been investigated as sensitisers in electro- and photoconductive compositions. There have also been some investigations of pyrylium-type compounds as anti-cancer agents. For example, in Japanese Laid Open Patent Application No. 64-52715, dimethylaminophenyl-pyridyl-thiopyrylium salt which has been substituted at the 2, 4 and 6 positions has been disclosed as an anti-cancer agent. Furthermore, in Japanese laid open Application No. 1-153683 there has been disclosed as an anti-cancer agent a 2,4,6-triphenylpyrylium or a 2,4,6-triphenyl thiopyrylium salt in which at least two hydrogen atoms of the phenyl group are substituted by dialkylamino groups. Japanese laid open Patent Application No. 1-153683 discloses compounds of the same general formula as in the present invention, and the synthesis of compounds of this type had already been reported by R. Wizinger et al (Helv. Chim. Acta., vol. 39, 5, 1956). However, none of these patent applications discloses that pyrylium compounds exhibit anti-cancer activity on selective absorption into living tissue and irradiation with light.

Typical examples of compounds represented by the formula [I] which can be used as the active ingredient in a medicament for the photochemical treatment of cancer according to the present invention are shown in Table 1 below. In addition, the light absorption characteristics of typical compounds selected from Table 1 are shown in Table 2. Almost all the compound shown in Table 2 have their own absorption peaks in the region 600 nm or above, and have molar absorption coefficients as large as $5-8.5 \times 10^4$ l/mol.cm which enables more efficient use to be made of the light in photochemical treatment. Furthermore, compound 1 in Table 2 has an absorption peak in the region below 600 nm, but it has sufficiently strong absorption that it still provides better treatment efficiency at wavelengths greater than 600 nm.

In a further feature of the invention, medicaments for the photochemical treatment of cancer include pyrylium compounds whose ring structure and/or resonance structure is altered to displace the absorption wavelength towards 1000 nm so that the medicament can be used for treatment of deeper regions of the living body.

The mechanism by which the present pyrylium compounds attack cancer cells on exposure to light is not clear.

However, the inventors have discovered that these compounds stain double stranded nucleic acid and it has therefore been postulated that the operation of the present pyrylium compounds involves attack on double stranded nucleic acid. It is therefore believed that the compounds of formula [I] when used for the photochemical treatment of cancer work by a different mechanism from that of the known porphyrin compounds. It is therefore possible that medicaments according to the invention will be effective for cancers which are different from those in which the porphyrin-containing medicament is effective.

A variety of methods may be used for administering the medicament of the present invention to living human or animal bodies. One such method is by injection in which case the medicament is formulated as an injectable solution in a sterile physiologically acceptable solvent. Suitable solvents include balanced saline solution, an aqueous buffer solution, a water-miscible organic solvent which can dissolve the compound of formula [I] such as dimethyl sulfoxide or ethanol, and a mixture of the aforesaid water miscible solvent, and a mixture of water containing dissolved materials. In the case of such a mixed solution, the ratio between the aqueous and the organic portions will be selected depending on the solubility properties of the compound of formula [I] and/or the place and manner in which the medicament is to be administered, and so that the injection maintains its characteristics and safety. For example there may be used a mixed solution in which the water component is mixed with 5–50% by volume of water miscible organic solvent. The medicament may be injected into a vein, an artery, into the abdominal cavity, through the skin or direct into a tumour. In addition, where the injectable material contains only a water miscible organic material as solvent, the injection is preferably carried out in portions of the body other than a vein or an artery.

The content of the compound represented by the formula [I] in the injectable solution can be selected depending upon the solubility of the compound, the method of injection, the place where the injection is to be administered and the amount of the compound to be given. For example, the content of the active compound may be in the range of from about 0.1 mg/ml to 10 mg/ml. Furthermore, the amount of medicament to be administered can be selected appropriately depending upon the conditions of the patient and the disease to be treated.

Some forms of the medicament according to the invention can also be given orally. Medicine for oral administration may be provided in known forms, for example in the forms of solutions, syrups, pills, capsules etc., using a suitable base material, solid diluent e.g. for making tablets, powders or capsules, or solvent for making syrups and elixirs. Medicaments for oral administration can be made by known methods. The content of the compound of formula [I] in a medicament for oral administration will be selected depending upon the patient to be treated and the disease to be treated and may, for example, be typically from 1–50 wt. %, particularly 5–20 wt. %. The active ingredients in the above compositions may be selected from the compounds listed in Table 1 below. The properties of some of the aforesaid compounds are as set out in Table 2 below.

TABLE 1

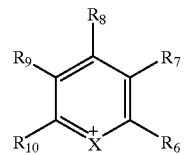

| Compd No. | X | Y | $R_i$ | L | A |
|---|---|---|---|---|---|
| 1 | O | $ClO_4$ or I | $R_6 = CH_3$<br>$R_7 = H$<br>$R_8 = \Phi\text{-}N(CH_3)_2$<br>$R_9 = H$<br>$R_{10} = A$ | | $\Phi\text{-}N(CH_3)_2$ |
| 2 | S | $ClO_4$ or I | $R_6 = CH_3$<br>$R_7 = H$<br>$R_8 = \Phi\text{-}N(CH_3)_2$<br>$R_9 = H$<br>$R_{10} = A$ | | $\Phi\text{-}N(CH_3)_2$ |
| 3 | O | $ClO_4$ or I | $R_6 = \Phi$<br>$R_7 = H$<br>$R_8 = A$<br>$R_9 = H$<br>$R_{10} = \Phi$ | | $\Phi\text{-}N(CH_3)_2$ |
| 4 | S | $ClO_4$ or I | $R_6 = \Phi$<br>$R_7 = H$<br>$R_8 = A$<br>$R_9 = H$<br>$R_{10} = \Phi$ | | $\Phi\text{-}N(CH_3)_2$ |
| 5 | O | $ClO_4$ or I | $R_6 = \Phi$<br>$R_7 = H$<br>$R_8 = L\text{-}A$<br>$R_9 = H$<br>$R_{10} = \Phi$ | General Formula [II]<br>n = 0<br>Z = H | $\Phi\text{-}N(CH_2CH_3)_2$ |
| 6 | S | $ClO_4$ or I | $R_6 = \Phi$<br>$R_7 = H$<br>$R_8 = L\text{-}A$<br>$R_9 = H$ | General Formula [II]<br>n = 0<br>Z = H | $\Phi\text{-}N(CH_2CH_3)_2$ |

TABLE 1-continued

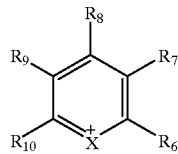

| Compd No. | X | Y | $R_i$ | L | A |
|---|---|---|---|---|---|
| 7 | O | ClO$_4$ or I | $R_6 = \Phi$<br>$R_7 = H$<br>$R_8 = \Phi$<br>$R_9 = H$<br>$R_{10} = L-A$ | General Formula [II]<br>n = 0<br>Z = H | $\Phi$-N(CH$_3$)$_2$ |
| 8 | S | ClO$_4$ or I | $R_6 = \Phi$<br>$R_7 = H$<br>$R_8 = \Phi$<br>$R_9 = H$<br>$R_{10} = L-A$ | General Formula [II]<br>n = 0<br>Z = H | $\Phi$-N(CH$_3$)$_2$ |
| 9 | O | ClO$_4$ or I | $R_6 = \Phi$<br>$R_7 = H$<br>$R_8 = L-A$<br>$R_9 = H$<br>$R_{10} = \Phi$ | General Formula [II]<br>n = 1<br>Z = H | $\Phi$-N(CH$_3$)$_2$ |
| 10 | S | ClO$_4$ or I | $R_6 = \Phi$<br>$R_7 = H$<br>$R_8 = L-A$<br>$R_9 = H$<br>$R_{10} = \Phi$ | General Formula [II]<br>n = 1<br>Z = H | $\Phi$-N(CH$_3$)$_2$ |
| 11 | O | ClO$_4$ or I | $R_6 = \Phi$<br>$R_7 = H$<br>$R_8 = L-A$<br>$R_9 = H$<br>$R_{10} = \Phi$ | General Formula [II]<br>n = 1<br>Z = (-)CH=CH-$\Phi$-N(CH$_3$)$_2$ | $\Phi$-N(CH$_3$)$_2$ |
| 12 | S | ClO$_4$ or I | $R_6 = \Phi$<br>$R_7 = H$<br>$R_8 = L-A$<br>$R_9 = H$<br>$R_{10} = \Phi$ | General Formula [II]<br>n = 1<br>Z = (-)CH=CH-$\Phi$-N(CH$_3$)$_2$ | $\Phi$-N(CH$_3$)$_2$ |
| 13 | O | ClO$_4$ or I | $R_6 = \Phi$<br>$R_7 = H$<br>$R_8 = L-A$<br>$R_9 = H$<br>$R_{10} = \Phi$ | General Formula [III]<br>n = 1 | $\Phi$-N(CH$_3$)$_2$ |
| 14 | S | ClO$_4$ or I | $R_6 = \Phi$<br>$R_7 = H$<br>$R_8 = L-A$<br>$R_9 = H$<br>$R_{10} = \Phi$ | General Formula [III]<br>n = 1 | $\Phi$-N(CH$_3$)$_2$ |
| 15 | O | ClO$_4$ or I | $R_6 = \Phi$<br>$R_7 = H$<br>$R_8 = L-A$<br>$R_9 = H$<br>$R_{10} = \Phi$ | General Formula [IV] | $\Phi$-N(CH$_2$CH$_3$)$_2$ |
| 16 | S | ClO$_4$ or I | $R_6 = \Phi$<br>$R_7 = H$<br>$R_8 = L-A$<br>$R_9 = H$<br>$R_{10} = \Phi$ | General Formula [IV] | $\Phi$-N(CH$_2$CH$_3$)$_2$ |
| 17 | O | ClO$_4$ or I | $R_6 = \Phi$<br>$R_7 = H$<br>$R_8 = \Phi$<br>$R_9 = H$<br>$R_{10} = L-A$ | General Formula [IV] | $\Phi$-N(CH$_2$CH$_3$)$_2$ |
| 18 | S | ClO$_4$ or I | $R_6 = \Phi$<br>$R_7 = H$<br>$R_8 = \Phi$<br>$R_9 = H$<br>$R_{10} = L-A$ | General Formula [IV] | $\Phi$-N(CH$_2$CH$_3$)$_2$ |

TABLE 1-continued

| Compd No. | X | Y | $R_i$ | L | A |
|---|---|---|---|---|---|
| 19 | O | $ClO_4$ or I | $R_6 = \Phi$<br>$R_7 = H$<br>$R_8 = \Phi$<br>$R_9 = H$<br>$R_{10} = L\text{-}A$ | General Formula [V] | |
| 20 | S | $ClO_4$ or I | $R_6 = \Phi$<br>$R_7 = H$<br>$R_8 = \Phi$<br>$R_9 = H$<br>$R_{10} = L\text{-}A$ | General Formula [V] | |
| 21 | O | $ClO_4$ or I | $R_6 = \Phi$<br>$R_7 = H$<br>$R_8 = \Phi$<br>$R_9 = H$<br>$R_{10} = L\text{-}A$ | General Formula [V] | |
| 22 | O | $ClO_4$ or I | $R_6 = \Phi$<br>$R_7 = H$<br>$R_8 = \Phi$<br>$R_9 = H$<br>$R_{10} = L\text{-}A$ | General Formula [VI] | |
| 23 | S | $ClO_4$ or I | $R_6 = \Phi$<br>$R_7 = H$<br>$R_8 = \Phi$<br>$R_9 = H$<br>$R_{10} = L\text{-}A$ | General Formula [VI] | |
| 24 | O | $ClO_4$ or I | $R_6 = \Phi$<br>$R_7 = H$<br>$R_8 = \Phi$<br>$R_9 = H$<br>$R_{10} = L\text{-}A$ | General Formula [VI] | |
| 25 | O | $ClO_4$ or I | $R_6 = \Phi$<br>$R_7 = H$<br>$R_8 = \Phi$<br>$R_9 = H$<br>$R_{10} = L\text{-}A$ | General Formula [II]<br>n = 0<br>Z = H | |

TABLE 1-continued

| Compd No. | X | Y | $R_i$ | L | A |
|---|---|---|---|---|---|
| 26 | S | $ClO_4$ or I | $R_6 = \Phi$<br>$R_7 = H$<br>$R_8 = \Phi$<br>$R_9 = H$<br>$R_{10} = L-A$ | General Formula [II]<br>n = 0<br>Z = H | |
| 27 | O | $ClO_4$ or I | $R_6 = \Phi$<br>$R_7 = H$<br>$R_8 = \Phi$<br>$R_9 = H$<br>$R_{10} = L-A$ | General Formula [II]<br>n = 0<br>Z = H | |
| 28 | S | $ClO_4$ or I | $R_6 = \Phi$<br>$R_7 = H$<br>$R_8 = \Phi$<br>$R_9 = H$<br>$R_{10} = L-A$ | General Formula [II]<br>n = 0<br>Z = H | |
| 29 | O | $ClO_4$ or I | $R_6 = \Phi$<br>$R_7 = H$<br>$R_8 = \Phi$<br>$R_9 = H$<br>$R_{10} = L-A$ | General Formula [II]<br>n = 0<br>Z = H | |
| 30 | O | $ClO_4$ or I | $R_6 = \Phi$<br>$R_7 = H$<br>$R_8 = L-A$<br>$R_9 = H$<br>$R_{10} = \Phi$ | General Formula [II]<br>n = 0<br>Z = H | |
| 31 | S | $ClO_4$ or I | $R_6 = \Phi$<br>$R_7 = H$<br>$R_8 = L-A$<br>$R_9 = H$<br>$R_{10} = \Phi$ | General Formula [II]<br>n = 0<br>Z = H | |
| 32 | O | $ClO_4$ or I | $R_6 = \Phi$<br>$R_7 = H$<br>$R_8 = L-A$<br>$R_9 = H$<br>$R_{10} = \Phi$ | General Formula [II]<br>n = 0<br>Z = H | |
| 33 | O or S | $ClO_4^-$ or $I^-$ | $R_6 = \Phi-N(CH_3)_2$<br>$R_7 = H$<br>$R_8 = A$ | | $\Phi-N(CH_3)_2$ |

TABLE 1-continued

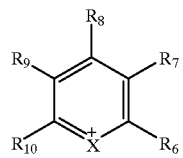

| Compd No. | X | Y | $R_i$ | L | A |
|---|---|---|---|---|---|
| | | | $R_9$ = H | | |
| | | | $R_{10}$ = Φ-N(CH$_3$)$_2$ | | |
| 34 | O or S | ClO$_4^-$ or I$^-$ | Same as Compd No. 33 | | CH$_3$ |
| 35 | O or S | ClO$_4^-$ or I$^-$ | " | | Φ-COOH |
| 36 | O or S | ClO$_4^-$ or I$^-$ | $R_6$ = Φ-N(CH$_3$)$_2$<br>$R_7$ = H<br>$R_8$ = L-A<br>$R_9$ = H<br>$R_{10}$ = Φ-N(CH$_3$)$_2$ | General Formula [II]<br>n = 0<br>Z = H<br>E | Φ-N(CH$_3$)$_2$ |
| 37 | O or S | ClO$_4^-$ or I$^-$ | Same as Compd No. 36 | General Formula [II]<br>n = 1<br>Z = H | Φ-N(CH$_3$)$_2$ |
| 38 | O or S | ClO$_4^-$ or I$^-$ | Same as Compd No. 36 | General Formula [III]<br>n = 1 | Φ-N(CH$_3$)$_2$ |
| 39 | O or S | ClO$_4^-$ or I$^-$ | " | General Formula [IV] | Φ-N(CH$_3$)$_2$ |
| 40 | O or S | ClO$_4^-$ or I$^-$ | " | General Formula [II]<br>n = 0<br>Z = H | Φ-COOH |
| 41 | O or S | ClO$_4^-$ or I$^-$ | " | General Formula [II]<br>n = 1<br>Z = H | -Φ-COOH |
| 42 | O or S | ClO$_4^-$ or I$^-$ | " | General Formula [III]<br>n = 1 | Φ-COOH |
| 43 | O or S | ClO$_4^-$ or I$^-$ | " | General Formula [IV] | Φ-COOH |
| 44 | O or S | I$^-$ or ClO$_4^-$ | $R_6$ = L-A<br>$R_7$ = H<br>$R_8$ = Φ-N(CH$_3$)$_2$<br>$R_9$ = H<br>$R_{10}$ = Φ-N(CH$_3$)$_2$ | General Formula [II]<br>n = 0<br>Z = H | Φ-N(CH$_3$)$_2$ |
| 45 | O or S | I$^-$ or ClO$_4^-$ | $R_6$ = L-A<br>$R_7$ = H<br>$R_8$ = Φ-N(CH$_3$)$_2$<br>$R_9$ = H<br>$R_{10}$ = Φ-N(CH$_3$)$_2$ | General Formula [II]<br>n = 1<br>Z = H | Φ-N(CH$_3$)$_2$ |
| 46 | O or S | I$^-$ or ClO$_4^-$ | $R_6$ = L-A<br>$R_7$ = H<br>$R_8$ = Φ-N(CH$_3$)$_2$<br>$R_9$ = H<br>$R_{10}$ = Φ-N(CH$_3$)$_2$ | General Formula [III]<br>n = 1 | Φ-N(CH$_3$)$_2$ |
| 47 | O or S | I$^-$ or ClO$_4^-$ | $R_6$ = L-A<br>$R_7$ = H<br>$R_8$ = Φ-N(CH$_3$)$_2$<br>$R_9$ = H<br>$R_{10}$ = Φ-N(CH$_3$)$_2$ | General Formula [IV] | Φ-N(CH$_3$)$_2$ |
| 48 | O or S | I$^-$ or ClO$_4^-$ | Same as Compd No. 44 | General Formula [II]<br>n = 0<br>Z = H | Φ-COOH |
| 49 | O or S | I$^-$ or ClO$_4^-$ | " | General Formula [II]<br>n = 1<br>Z = H | Φ-COOH |
| 50 | O or S | I$^-$ or ClO$_4^-$ | " | General Formula [III]<br>n = 1 | Φ-COOH |
| 51 | O or S | I$^-$ or ClO$_4^-$ | " | General Formula [II] | Φ-COOH |
| 52 | O | I$^-$ | $R_6$ = A | | —COOH |

TABLE 1-continued

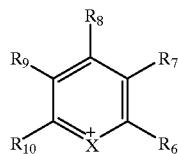

| Compd No. | X | Y | $R_i$ | L | A |
|---|---|---|---|---|---|
| | or S | or $ClO_4^-$ | $R_7$ = H<br>$R_8$ = Φ-N(CH$_3$)$_2$<br>$R_9$ = H<br>$R_{10}$ = Φ-N(CH$_3$)$_2$ | | |
| 53 | O or S | I$^-$ or $ClO_4^-$ | $R_6$ = A<br>$R_7$ = H<br>$R_8$ = Φ-N(CH$_3$)$_2$<br>$R_9$ = H<br>$R_{10}$ = Φ-N(CH$_3$)$_2$ | | -Φ-COOH |
| 54 | O or S | I$^-$ or $ClO_4^-$ | $R_6$ = Φ<br>$R_7$ = H<br>$R_8$ = Φ-N(CH$_3$)$_2$<br>$R_9$ = H<br>$R_{10}$ = Φ-N(CH$_3$)$_2$ | | |
| 55 | O or S | I$^-$ or $ClO_4^-$ | $R_6$ = Φ-N(CH$_3$)$_2$<br>$R_7$ = H<br>$R_8$ = Φ<br>$R_9$ = H<br>$R_{10}$ = Φ-N(CH$_3$)$_2$ | | |

TABLE 2

| | Absorption ($\lambda_{max}$) Peak | | Molar absorption coefficient ($\epsilon \times 10^{-4}$ l/mol · cm) |
|---|---|---|---|
| Compound No. | Under no existence of DNA | Under existence of DNA | $\epsilon$ |
| 1 | 540 nm | 580 nm | 8.46 |
| 2 | 580 nm | 620 nm | 4.95 |
| 3 | 535 nm | 570 nm | 7.08 |
| 4 | 575 nm | 610 nm | 5.39 |
| 6 | 660 nm | 690 nm | — |
| 8 | 650 nm | 670 nm | — |
| 9 | 660 nm | 720 nm | — |
| 11 | 625 nm | 660 nm | — |
| 15 | 670 nm | 680 nm | — |
| 16 | 690 nm | 720 nm | 7.55 |
| 17 | 690 nm | 720 nm | — |

The invention will be further described by way of example with reference to the following Examples.

SYNTHESIS EXAMPLE 1

100 ml of acetic anhydride was mixed with 30 ml of concentrated sulfuric acid with cooling, and the resulting mixture was then heated for three hours on a water bath, while maintaining it at 80° C. Next, 20 ml of acetic anhydride and 30 ml of p-dimethylamino acetophenone were added thereto at room temperature, and the temperature of the solution was then raised up to 45° C., followed by stirring for 24 hours to carry out reaction, Afterward, ethanol was added to the reacted solution, the amount of ethanol being equal to that of the reacted solution. This solution was cooled, and an aqueous pottasium iodide solution was then added thereto to precipitate crude crystals. Next, the crystals were collected by filtration, and then recrystallised from a mixture of ethanol and ether (a volume ratio=1:4) to obtain green crystals of 2-methyl-4,6-bis-(4-N,N-dimethylaminophenyl) pyrylium iodide (Compound No. 1 in Table 1 wherein Y is I).

Analytical results of the obtained Compound No. 1 (Y=I) melting point=254–257° C.

UV/Visual (CH$_3$CN $\epsilon \times 10^{-4}$) $\lambda_{max}$=444 nm (2.43), 550 nm (8.24)

NMR ($^1$H, DMSO) δ ppm: 8.3737 (1H, s) 8.2729 (1H d, J=9.0 Hz), 8.1795 (1H, d, J=9.0 Hz), 7.8864 (1H, s), 6.9117 (4H, t, J$_{AB}$=J$_{BC}$=9.77), 3.1829 (6H, s), 3.1340 (6H, s), 2.6809 (3H, s)

FAB mass m/z 333

IR (KBr) υV cm$^{-1}$: 1645, 1610 (sh), 1580 (s), 1490 (s), 1270, 1200, 1160

Furthermore, the same procedure as described above was carried out except that the aqueous potassium iodide solution was replaced with an aqueous perchloric acid solution, to obtain 2-methyl-4,6-bis-(4-N,N-dimethylaminophenyl) pyrylium perchlorate (compound 1 in Table 1 wherein Y is ClO$_4$).

SYNTHESIS EXAMPLE 2

20 g of sodium sulfide nonahydrate was dissolved in ion-exchanged water so as to bring the total volume to 50 ml. Next, 7 g of sodium hydrocarbonate was added to and dissolved in this solution, and 50 ml of ethanol was further added thereto under ice cooling, followed by stirring at room temperature for 30 minutes. The precipitated sodium carbonate was collected by filtration, and then washed with 25 ml of ethanol. Afterward, the filtrate was mixed with the washing liquid to obtain about 125 ml of the water-ethanol solution of sodium hydrogen sulfide.

Next, 0.92 g of 2-methyl-4,6-bis-(4-N,N-dimethylaminophenyl)pyrylium iodide obtained in Synthesis Example 1 was dissolved in 20 ml of DMSO, and 5 ml of the previously prepared water-ethanol solution of sodium hydrogen sulfide was then added to the resulting solution, followed by stirring at room temperature for 5 minutes. After the stirring, 0.75 ml of hydoriodic acid was added thereto, and the solution was further stirred for 5 minutes. Subsequently, dichloromethane extraction and silica gel column purification were carried out in usual manner, followed by recrystallization in an ethanol-ether mixed solution (a volume ratio=1:4), to obtain the crystals of 2-methyl-4,6-bis-(4-N,N-dimethylaminopheynl)thiopyrylium iodide (Compound No. 2 in Table 1 wherein Y is I).

Analytical results of the obtained Compound No. 2=(Y=1):

Melting point: 246–248° C.

UV/visual (CH$_3$CN $\epsilon \times 10^{-4}$) λmax: 495 nm (2.50), 587 nm (4.95)

NMR ($^1$H, DMSO) δ ppm: 8.5679 (1H, s), 8.84323 (1H, s), 8.2436 (2H, d, J=9.27 Hz), 7.9786 (2H, d, J=9.28), 6.8959 (4H, t, J$_{AB}$=J$_{BC}$=9.28), 3.1756 (6H, s), 3.1157 (6H, s), 2.8323 (3H, s)

FAB mass m/z 349

IR (KBr) υ cm$^{-1}$:1600 (s), 1560 (s), 1460 (s), 1370 (s), 1260 (s), 1160 (s)

Furthermore, the same procedure as described above was carried out except that hydoriodic acid was replaced with an aqueous perchloric acid solution, to obtain 2-methyl-4,6-bis-(4-N,N-dimethylaminophenyl)-thiopyrylium perchlorate (Compound No. 2 in Table 1 wherein Y is ClO$_4$).

Further compounds No. 3 to 55 shown in Table 1 were prepared. In Table I Φ is a p-phenylene group

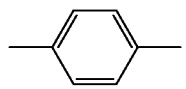

or a phenyl group.

These compounds were synthesised in the following known methods. In this connection, the typical reaction operations were done in accordance with usual procedures.

A compound 7 was obtained by synthesising the compound [i]

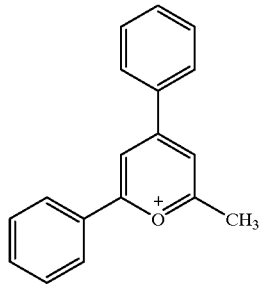

[i]

in accordance with a process described in W. Foerst et al., "New Methods of Preparative Organic Chemistry", Acad. Press (1964)"; reacting the synthesised compound [i] with

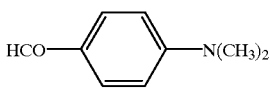

(p-N,N-dimethylaninobenzaldehyde) to form a compound; and then reacting the formed compound with desired anions.

A compound 17 was obtained by reacting the above-mentioned compound [i] with

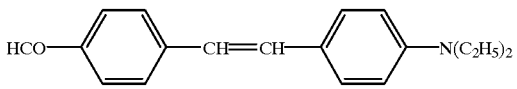

(p-diethylaminostyrylbenzaldehyde) to form a compound; and then reacting the formed compound with desired anions.

Compounds 8 and 18 were synthesised by reacting the above-mentioned compound [i] with sodium hydrogen sulfide to form a compound [ii]

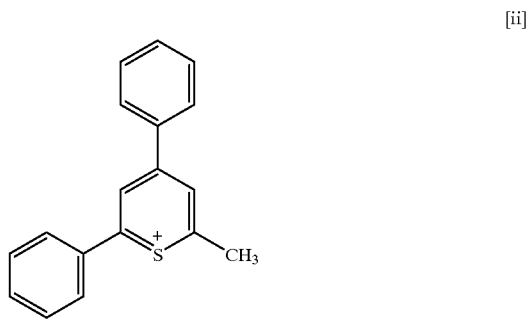

[ii]

and then treating this compound [ii] in the same manner as in the compounds 7 and 17.

A compound 5 was obtained by synthesising a compound [iii]

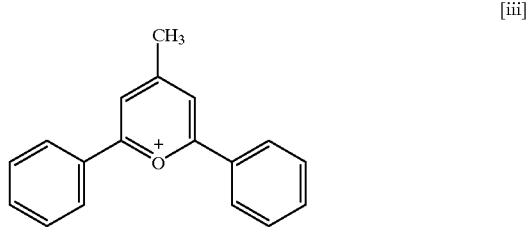

[iii]

from acetophenone and acetaldehyde in accordance with a process described in R. Wizinger et al., Helv. Chim. Acta., 39, p. 217 (1956) via the following route:

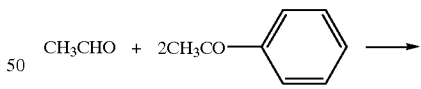

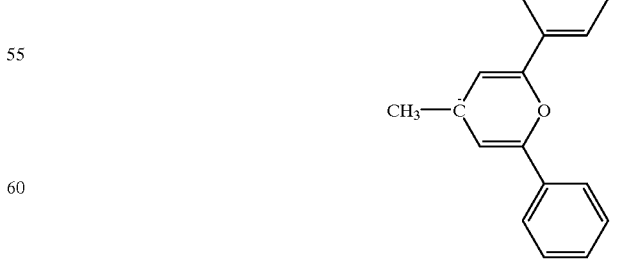

reacting this compound [iii] with p-dimethylaminobenzaldehyde to form a compound; and then reacting the formed compound with desired anions. A compound 15 was obtained by the same procedure as in the synthesis of the compound 5 except that p-dimethylaminobenzaldehyde was replaced with p-dimethylaminostyrylbenzaldehyde. A compound 9 was obtained by the same procedure as in the synthesis of the compound 5 except that p-dimethylaminobenzaldehyde was replaced with p-dimethylaminocinnamic aldehyde. A compound 11 was obtained by the same procedure as in the synthesis of the compound 5 except that p-dimethylaminobenzaldehyde was replaced with the following compound:

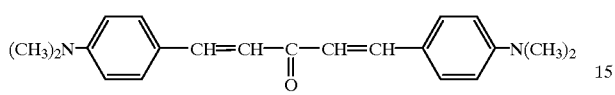

[iii]

Compounds 6, 16, 10 and 12 were obtained by the same procedure as in the compound 5, 15 and 9, respectively, except tht the above-mentioned compound [iii] was replaced with a compound [iv]

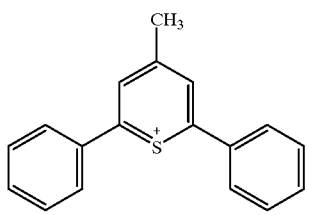

[iv]

which was obtained by reacting the above-mentioned compound [iii] with sodium hydrogen sulfide.

A compound 4 was obtained by forming the compound 3 in the same manner as in the synthesis of the above-mentioned compound [iii] except that a raw material acetaldehyde was replaced with p-dimethylaminobenzaldehyde; reacting with the compound 3 with sodium hydrogen sulfide to form a compound; and then reacting the formed compound with desired anions.

A compound 13 was obtained by forming a compound [v]

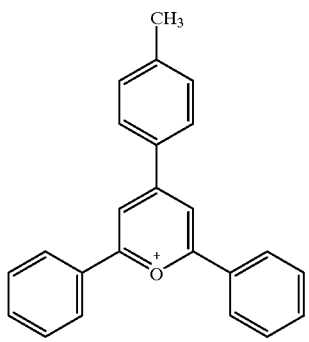

[v]

from p-methylbenzaldehyde and acetophenone in like manner; reacting the compound [v] with p-dimethylaminobenzaldehyde to form a compound; and then reacting the formed compound with desired anions.

A compound 14 was obtained by the same procedure as in the compound 13 except that the above-mentioned compound [v] was replaced with a compound [vi]

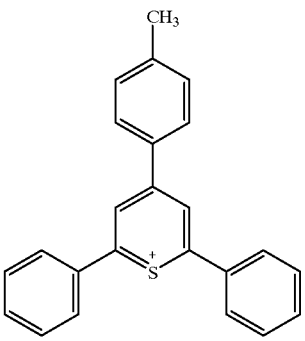

[vi]

which was formed by reacting the compound [v] with sodium hydrogen sulfide.

Compounds 19, 20 and 21 were each obtained by reacting the compound [i] or [ii], or the compound 1 or 2 and

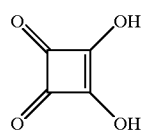

and then reacting the resulting compound with desired anions. Compounds 22, 23 and 24 were each obtained by reacting the compound [i] or [ii], or the compound 1 or 2 and

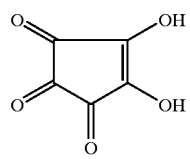

and then reacting the resulting compound with desired anions. Compounds 25 and 26 were each obtained by reacting the compounds [i] or [ii] with

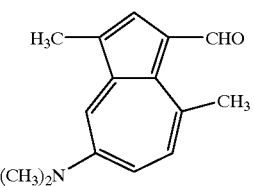

and then reacting the resulting compound with desired anions. Compounds 27, 28 and 29 were each obtained by reacting the compound [i] or [ii], or the compound 1 or 2 and triethoxymethane [$HC(OC_2H_5)_3$]; and then reacting the resulting compound with desired anions. Compounds 30, 31 and 32 where synthesised by reacting dimethylamino derivatives of the above-mentioned compounds [iii] and [iv] synthesised from p-dimethylamino acetophenone in the same manner as in the -compounds [iii] and [iv], the compound [iii] or [iv] and triethoxymethane; and further reacting the resulting compound with desired anions.

Each of the compounds 33 to 55 was synthesized in a manner as shown in the following:

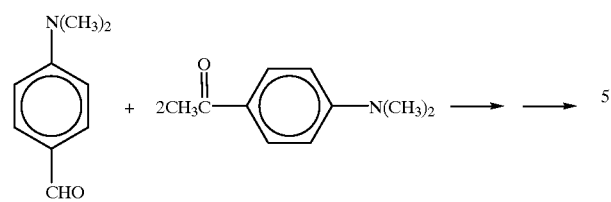
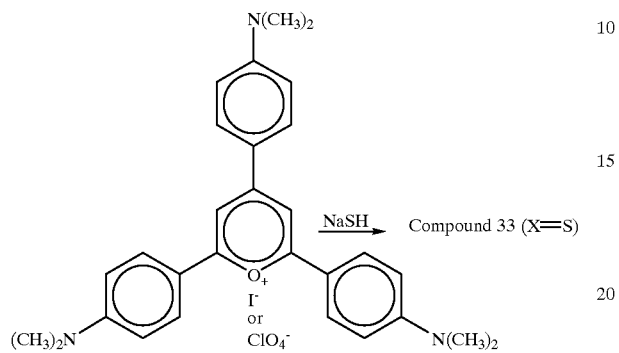
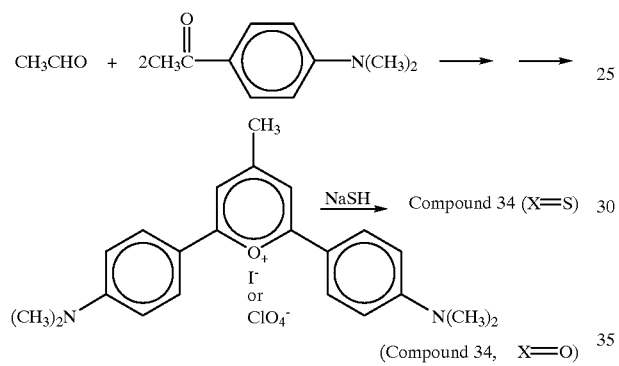
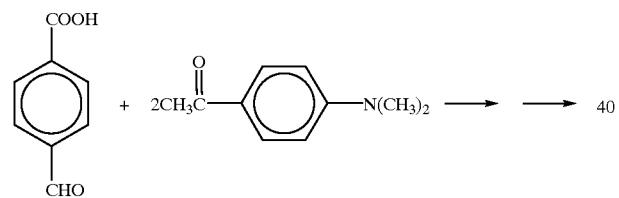
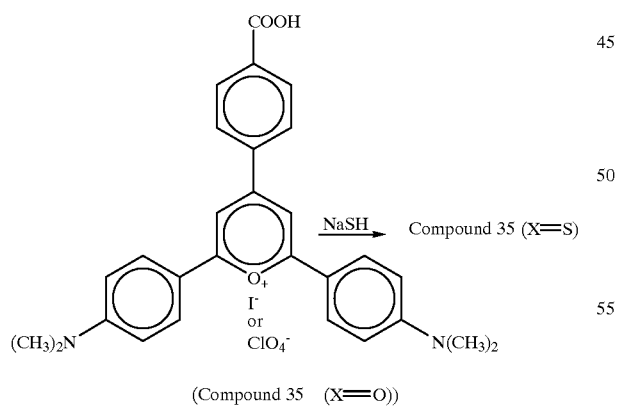
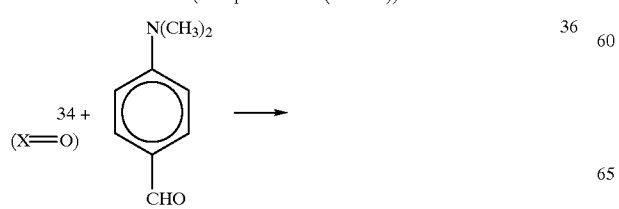
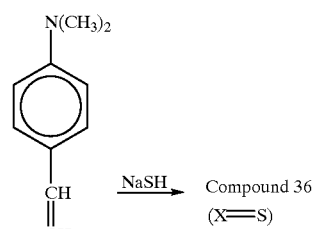
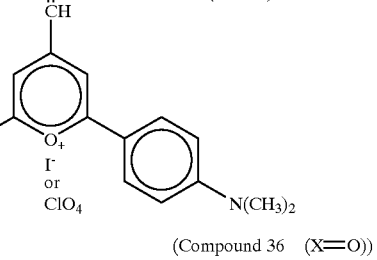
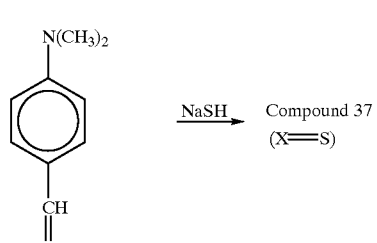
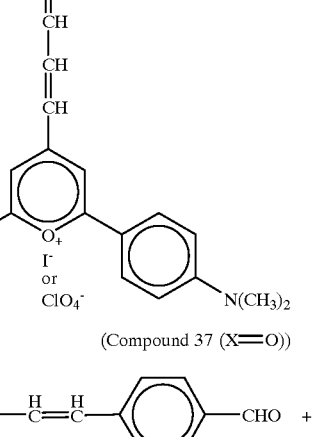
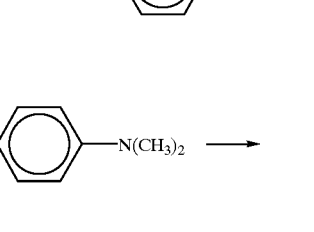

-continued

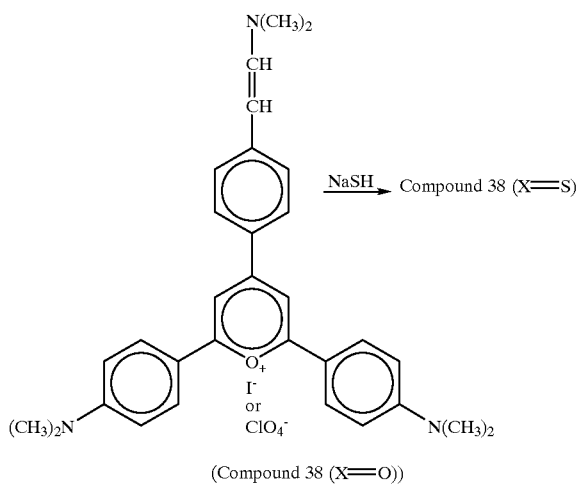

(Compound 38 (X═O))

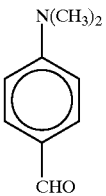

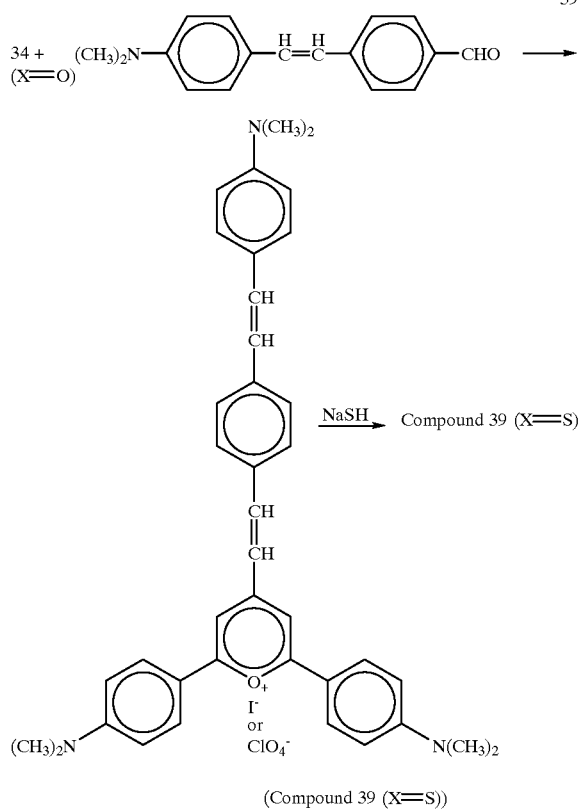

(Compound 39 (X═S))

This compound was synthesised in the same manner as 36, except that

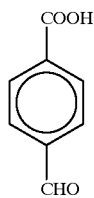

was employed instead of the material

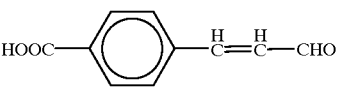

This compound was synthesised in the same manner as 37, except that

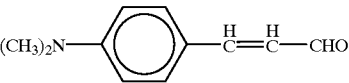

was employed instead of the material

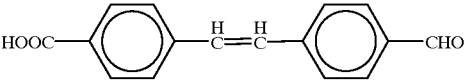

42 This compound was synthesised in the same manner as 38, except that

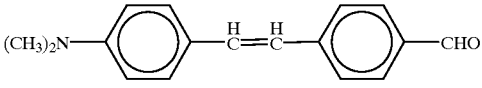

was employed instead of the material

43 This compound was synthesised in the same manner as 39, except that

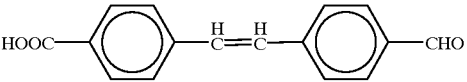

was employed instead of the material

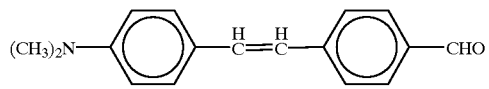
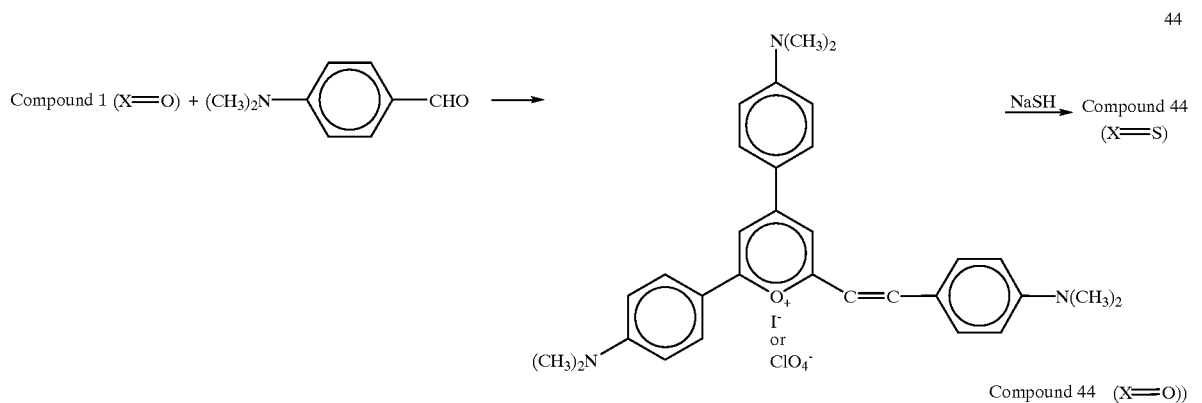
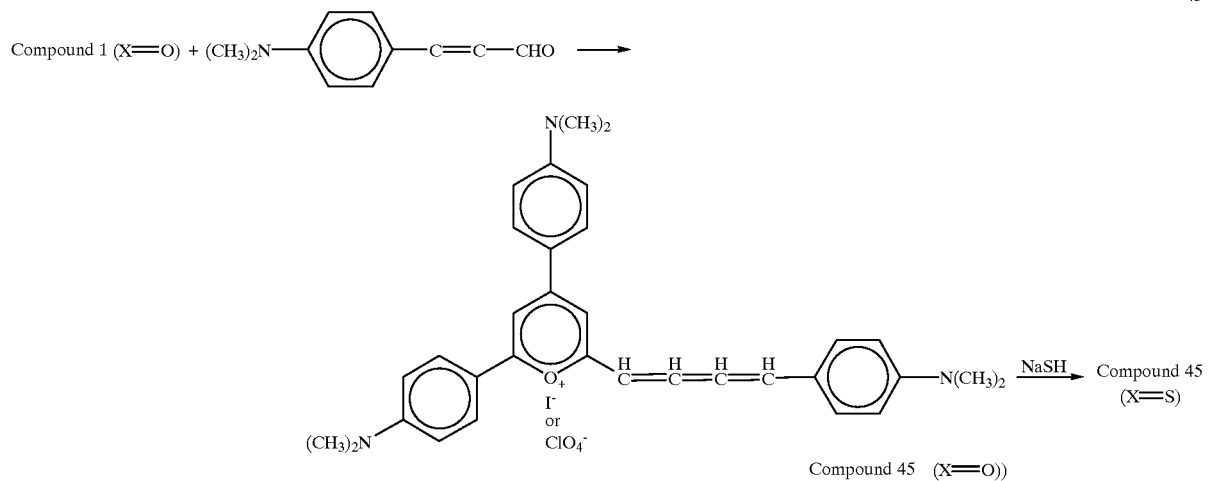
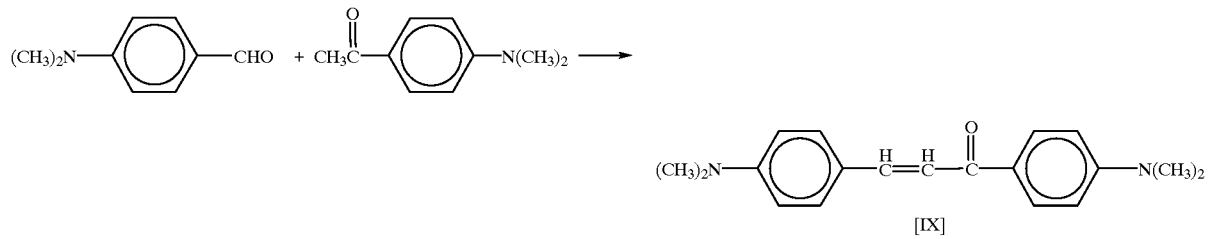
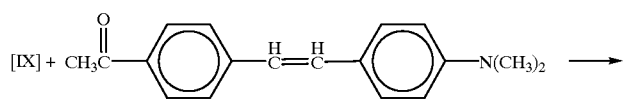

-continued

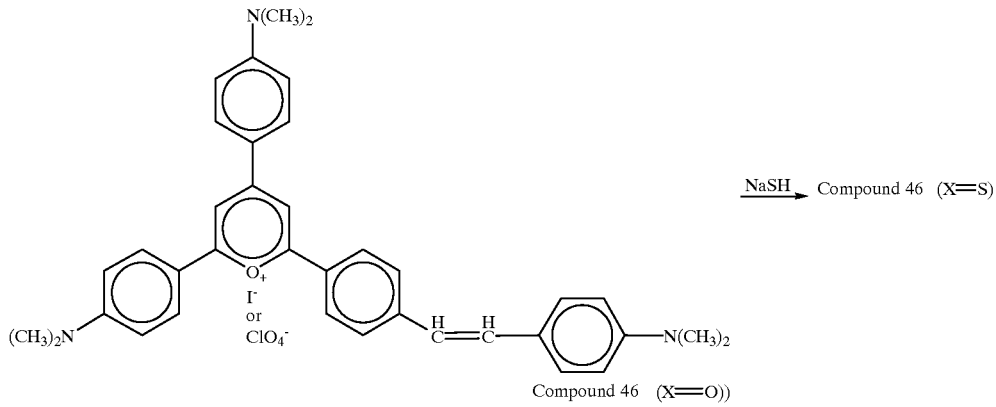

Compound 46 (X=O))

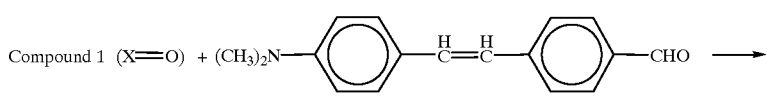

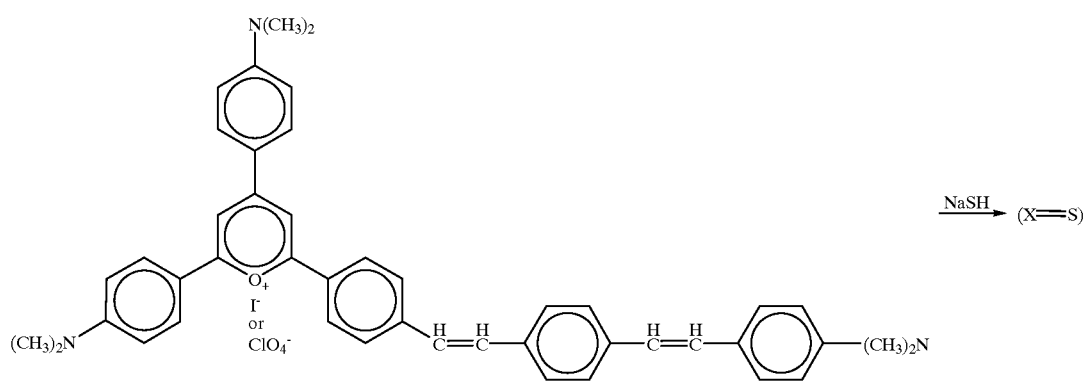

48 This compound was synthesised in the same manner as 44, except that

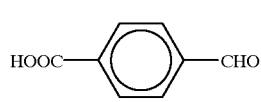

was employed instead of the material

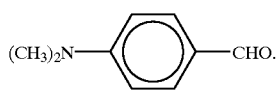

49 This compound was synthesised in the same manner as 45, except that

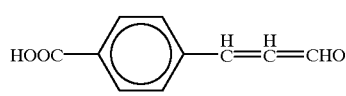

was employed instead of the material

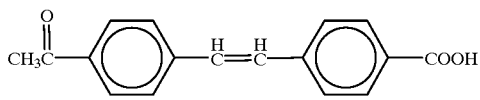

50 This compound was synthesised in the same manner as 46, except that

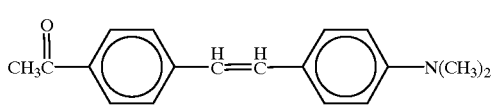

was employed instead of the material

51 This compound was synthesised in the same manner as 47, except that

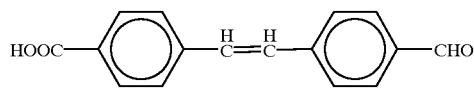

was employed instead of the material

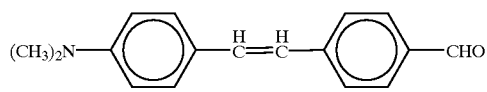

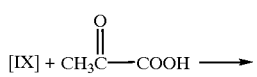

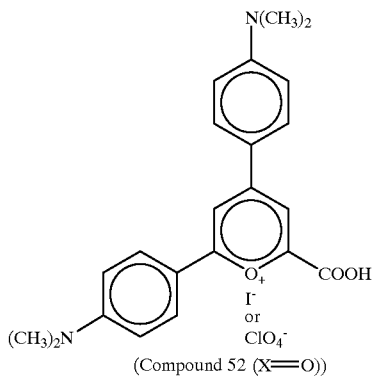

(Compound 52 (X=O))

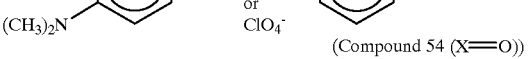

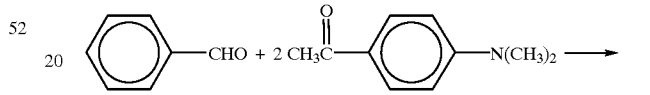

(Compound 54 (X=O))

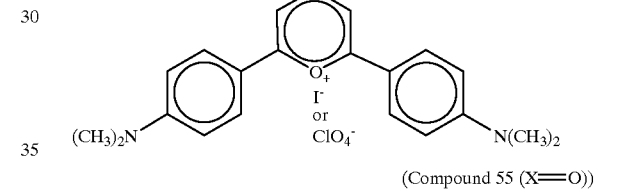

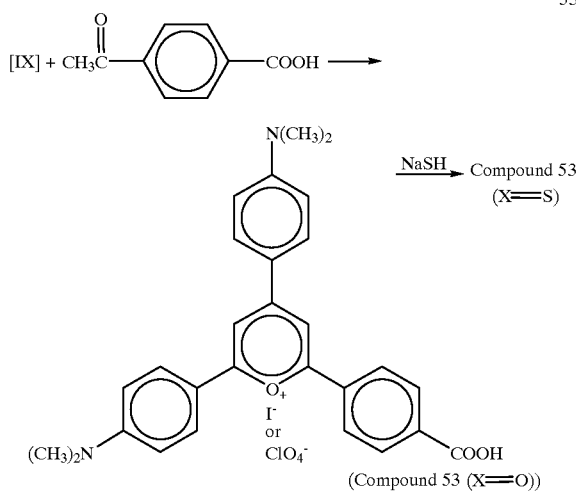

(Compound 55 (X=O))

53

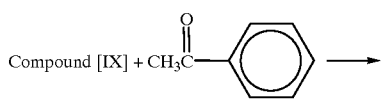

(Compound 53 (X=O))

54

EXAMPLE 1

L-929 cells which are typical cultured cancer cells from mice were planted onto a culture medium containing E-MEM+10% FCS. The density of the cells in the medium was $10^6$ cells/dish (20 ml). Thereafter, the cells were maintained at 37° C. and cultured for 36 hours. Four such cultures using the same medium were prepared. Then compound 1 (Y=I) was added to each of the above cultured media and the concentration of the compound 1 was varied from sample to sample as shown in Table 3. Then radiation of wavelength from 560–610 nm to which the compound 1 is responsive was supplied using a fluorescence microscope for the interval of time indicated in Table 3. Thereafter, each medium was cultured for 12 hours, after which the cells were observed using a microscope. The percentage of the cells which had died in each sample was estimated and is shown in Table 3. As is apparent from this table, the compound 1 in a concentration in the medium of 0.1–0.5 μg/ml is effective to kill cancer cells on irradiation for a period of 1–5 minutes. It has been found that uptake of compound 1 by the cancer cells is rapid. Furthermore, cancer cells which were treated by the compound of Example 1 and not irradiated, and cancer cells which were irradiated without addition of the medicament were not killed and continued to grow in culture under the test conditions.

TABLE 3

| Irradiated Time | Concentration of the Compound 1 (μg/ml) | | | |
|---|---|---|---|---|
| | 0.05 | 0.1 | 0.25 | 0.5 |
| 5 (min) | 20~30 (%) | 100 (%) | 100 (%) | 100 (%) |
| 3 | — | 70~80 | ~100 | ~100 |
| 1 | — | — | 50~60 | ~90 |

EXAMPLE 2

The same test as in Example 1 was carried out except that the active compound used was compound 2 (Y=I) instead of compound 1. The amount of compound 2 which was administered to the cells is shown in Table 4 and the percentage of cells which died for the various irradiation times is also indicated. The light used to irradiate the cells at a wavelength of 600–650 nm.

The results shown in Table 4 indicate that compound 2 has a greater killing effect than compound 1 against cancer cells. It was also found that cancer cells not subjected to compound 2 and irradiated, and such cells which had been subjected to the compound but not irradiated were not killed and continued to grow in culture.

TABLE 4

| Irradiated Time | Concentration of the Compound 2 (μg/ml) | | | |
|---|---|---|---|---|
| | 0.025 | 0.05 | 0.075 | 0.1 |
| 5 (min) | ~50 (%) | 100 (%) | 100 (%) | 100 (%) |
| 3 | — | 80 | 100 | 100 |
| 1 | — | ~10 | 80 | 100 |

EXAMPLE 3

The same test was carried out as in Example 1 except that the compound 16 (Y=I) was used in place of the compound 1. The cells were irradiated with light of wavelength 700–750 nm. The results are shown in Table 5. In that table, it is apparent that compound 16 is as active against cancer cells as the compound 2, and that radiation of wavelength 720 nm can be used for photochemical treatment of the cancer cells. Again, cancer cells to which the compound 16 was administered but were not subject to radiation, and cancer cells to which the compound 16 was not administered and were subjected to the radiation at 700–750 nm were not killed and continued to grow in culture.

TABLE 5

| Irradiated Time | Concentration of the Compound 16 (μg/ml) | | | |
|---|---|---|---|---|
| | 0.025 | 0.05 | 0.075 | 0.1 |
| 5 (min) | ~30 (%) | 100 (%) | 100 (%) | 100 (%) |
| 3 | — | 70 | ~90 | 100 |
| 1 | — | — | 80 | 100 |

Examples of Medicaments

EXAMPLE 4

The compound 1 (Y=I) was dissolved at a concentration of 1 mg/ml into balanced saline solution to give an injectable solution.

EXAMPLE 5

The compound 2 (Y=I) was dissolved into a mixed solution containing 80 volume % of balanced saline solution and 20 volume % of ethanol to give an injectable solution. The concentration was 5 mg/ml.

Acute Toxicity Test

EXAMPLE 6

The compound 1 (Y=I) was dissolved into a balanced saline solution and was injected into each of 2 nude mice of weight 200–400 g through a vein in the log of the mouse. The amount of solution injected was 1 mg to 1 kg of the weight of each mouse. Subsequent observation of the mice indicated no adverse effects, and they remained in satisfactory health after the injection.

EXAMPLE 7

The toxicity test of Example 6 was repeated except that the compound 2 was used in place of the compound 1. Again, observation of the mice indicated no ill effects, and the mice remained in good health after the injection.

EXAMPLE 8

The test of Example 6 was repeated except that the compound 1 (Y=I) was dissolved in dimethyl sulfoxide. The amount of solution injected was 1 mg per 1 kg of the mouse's weight. Subsequent injections on further groups of mice were carried out at 5 mg per 1 kg of the mouse's weight and 25 mg per 1 kg of the mouse's weight. No adverse effect on the mice was observed, and they continued to be in good health after the injection.

EXAMPLE 9

The same test as in Example 8 was carried out except that the active ingredient was compound 2 (Y=I) instead of compound 1. Again, no ill effects were observed in the mice who continued to thrive after the injection.

The results of the tests in Examples 6 to 9 indicate that the compounds tested have low acute toxicity.

Treatment of Cancer Cells in a Living Body

EXAMPLE 10

Ten nude mice having weight 200–400 g were selected, and they were separated into five groups referred to as A, B, C, D and E, each containing two nude mice. Each of the mice was inoculated on its back with KATO III, which is a culture of stomach cancer cells from a human patient. The cancer cells were inoculated into the central part of the back of each mouse, after which the mice were kept for ten days. It was found that the cancer in each mouse had grown to a size of about 5mm width, about 5mm length and about 3mm height. The mice in groups A, B and E were injected with the compound 1 (Y=I) in balanced saline solution through a vein in the leg. The amount of compound 1 which was administered to each mouse was 1 mg per 1 kg of the mouse's weight. Thereafter, the cancerous growth in each mouse in the group A and C was irradiated with white light in which the radiation of wavelength 400 nm or less and radiation of wavelength 1000 nm or above was filtered out. In group E, a part of every mouse's back was irradiated with the white light. In each case the amount of irradiation was 50J. Thereafter, the cancerous region of each mouse in the group A to D was observed and the skin of each mouse in the group E was observed. The results are as shown in Table 6.

EXAMPLE 11

The same test as in Example 10 was carried out except that the compound 2 was used in place of the compound 1. The results are shown in Table 7. The results given in Tables 6 and 7 indicate that compound 1 and compound 2 are effective in the photochemical treatment of human cancer cells growing in live mice. However, when the mice in group E or E' were irradiated, no change was observed so that it was apparent that the affinity of compound 1 and compound 2 for the cancer cells was different from the affinity of compound 1 and compound 2 for normal cells.

TABLE 6

(Compound 1)

| | | | | | Size of Cancer (width x lenth x height) | | | |
|---|---|---|---|---|---|---|---|---|
| Mouse No. | Inocculation of Cancer | Medication of Compound 1 | Irradiation | Before the Cure | 3 days after the Cure | After 7 days | After 14 days | After 28 days |
| A1 | o | o | o | 7 x 6 x 4 (mm) | 7 x 6 x 4 (mm) | 5 x 5 x 2 (mm) | 3 x 2 x 1 (mm) | 1 x 1 x 0 (mm) |
| A2 | o | o | o | 5 x 5 x 3 (mm) | 5 x 5 x 2 (mm) | 4 x 4 x 1 (mm) | 2 x 2 x 0 (mm) | *1 (mm) |
| B1 | o | o | — | 6 x 6 x 4 | 6 x 7 x 4 | 9 x 9 x 6 | 16 x 13 x 10 | 22 x 18 x 13 |
| B2 | o | o | — | 5 x 6 x 3 | 6 x 7 x 3 | 9 x 11 x 5 | 15 x 16 x 8 | 21 x 23 x 10 |
| C1 | o | — | o | 8 x 5 x 3 | 8 x 6 x 3 | 11 x 7 x 4 | 16 x 10 x 5 | 22 x 16 x 8 |
| C2 | o | — | o | 4 x 5 x 2 | 4 x 5 x 2 | 5 x 6 x 2 | 8 x 10 x 3 | 13 x 15 x 5 |
| D1 | o | — | — | 5 x 5 x 3 | 6 x 6 x 4 | 9 x 9 x 6 | 13 x 10 x 7 | 18 x 14 x 10 |
| D2 | o | — | — | 5 x 6 x 4 | 7 x 7 x 4 | 9 x 11 x 6 | 17 x 15 x 9 | 21 x 19 x 13 |
| E1 | — | o | o | | | No Change | | |
| E2 | — | o | o | | | No Change | | |

*1: the cancered part could not nearly be distinguished from its surrounding

TABLE 7

(Compound 2)

| | | | | | Size of Cancer (width x length x height) | | | |
|---|---|---|---|---|---|---|---|---|
| Mouse No. | Inocculation of Cancer | Medication of Compound 1 | Irradiation | Before the Cure | 3 days after the Cure | After 7 days | After 14 days | After 28 days |
| A' 1 | o | o | o | 5 x 4 x 4 (mm) | 5 x 4 x 4 (mm) | 3 x 2 x 1 (mm) | 1 x 1 x 0 (mm) | *2 (mm) |
| A' 2 | o | o | o | 5 x 5 x 3 (mm) | 5 x 5 x 3 (mm) | 2 x 2 x 1 (mm) | *1 (mm) | *2 (mm) |
| B' 1 | o | o | — | 6 x 8 x 5 | 8 x 9 x 7 | 11 x 10 x 8 | 17 x 17 x 11 | 21 x 21 x 14 |
| B' 2 | o | o | — | 7 x 6 x 4 | 7 x 8 x 5 | 9 x 10 x 5 | 12 x 14 x 7 | 19 x 17 x 11 |
| C' 1 | o | — | o | 6 x 4 x 3 | 6 x 6 x 3 | 8 x 8 x 4 | 10 x 12 x 6 | 18 x 15 x 8 |
| C' 2 | o | — | o | 8 x 7 x 4 | 9 x 9 x 5 | 11 x 12 x 7 | 18 x 16 x 10 | 22 x 21 x 12 |
| D' 1 | o | — | — | 5 x 7 x 4 | 6 x 8 x 4 | 8 x 10 x 5 | 11 x 12 x 8 | 16 x 18 x 10 |
| D' 2 | o | — | — | 4 x 6 x 3 | 5 x 6 x 3 | 6 x 6 x 5 | 7 x 8 x 6 | 12 x 14 x 8 |
| E' 1 | — | o | o | | | No Change | | |
| E' 2 | — | o | o | | | No Change | | |

*1 Vestige remained at the cancered part
*2 The cancered part could not nearly be distinguished from its surrounding

EXAMPLE 12

Four nude mice of weight 200–400 g were selected and were separated into groups X and Y, each containing two mice. Next, KATO III was inoculated into every mouse in the same way as in Example 10, after which the mice were kept for three weeks to fix the cancer cells. After three weeks the cancer in each mouse had grown and the size of the cancer was about 13 mm wide, 13 mm long and about 8 mm high. Next the mice in group X were injected via the leg with a balanced saline solution of the compound 1, and the mice in Group Y were injected with a balanced saline solution of the compound 16 via the leg. The dose of the compound 1 or 16 was adjusted to be 1 mg of the compound 1 or the compound 16 per 1 kg of the mouse's weight. Subsequently, the mice in group X were irradiated with radiation of wavelength 580 nm (half-width=20 nm) which was separated by means of a filter, and the mice in group Y were irradiated with radiation having a wavelength 720 nm (half-width=20 nm) which was separated with a filter. The amount of energy irradiated was 10J. One day after the irradiation the depth of the tumour which had become necrotic was measured. The results are as shown in Table 8, from which it is apparent that treatment with the compound whose absorption wavelength is longer by means of radiation of appropriate long wavelength can treat deeper parts of the living body.

TABLE 8

| Mouse No. | Compound | Deepness of died tumour |
|---|---|---|
| $X_1$ | 1 | 4.5 (mm) |
| $X_2$ | 1 | 4.8 |
| $Y_1$ | 16 | 7.5 |
| $Y_2$ | 16 | 7.7 |

The above results suggest that cancer cells can be treated with a medicament as set out herein, which is of completely different structure from known porphyrin-type photochemical medicaments. The treatment has been found to be particularly effective using pyrylium-type compounds having an absorption maximum in the range 600–1000 nm and having strong absorption strength. Furthermore, the salts of the present pyrylium-type compounds are readily absorbed by cells of the living body, including in particular some types at least of cancer cell so that the treatment can be carried out effectively. A selection of the substituent groups enables the absorption peak wavelength to be adjusted within the range 600–1000 nm so that the wavelength of the radiation required for treatment can also be selected.

What is claimed is:

1. A method for the treatment of human and animal cancer cells sensitive to treatment with the compounds below, which comprises administering to said human or animal a therapeutically effective quantity of a compound represented by the formula:

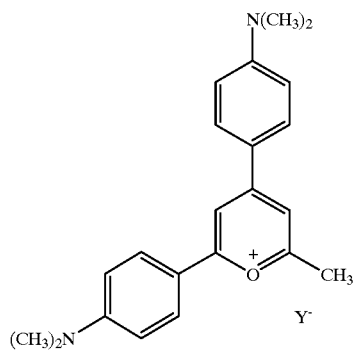

wherein $Y^-$ is an anion, and irradiating the cancer cells with light of a wavelength of at least 600 nm, the light being effectively absorbed by said compound for a period of time sufficient to induce death of the cancer cells.

2. The method according to claim 1, wherein Y is $ClO_4$.

3. The method according to claim 1, wherein Y is I.

4. A method for the treatment of human and animal cancer cells sensitive to treatment with a therapeutically effective quantity of the compounds below, which comprises:

adding to the cancer cells a compound represented by the formula:

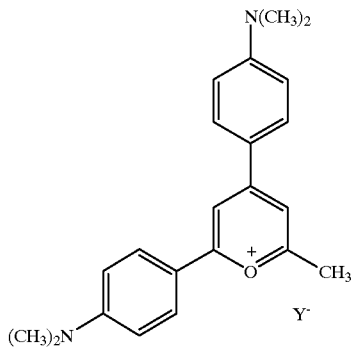

wherein $Y^-$ is an anion, and irradiating the cancer cells with light of a wavelength of at least 600 nm, the light being absorbed by said compound in the presence of DNA, for a period of time sufficient to induce death of the cancer cells.

5. The method according to claim 4, wherein the Y is $ClO_4$.

6. The method according to claim 4, wherein Y is I.

7. A method for the treatment of human and animal cancer sensitive to treatment with the compounds below, which comprises:

(a) administrating to said human or animal a therapeutically effective quantity of one of the following compounds:

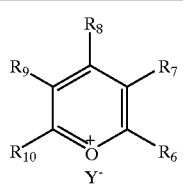

| Y | $R_i$ | L | A |
|---|---|---|---|
| $ClO_4$ or | $R_6 = CH_3$ $R_7 = H$ | | $\Phi\text{-}N(CH_3)_2$ |

-continued

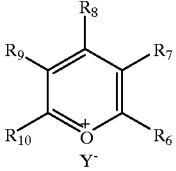

| Y | R$_i$ | L | A |
|---|---|---|---|
| I | R$_8$ = Φ-N(CH$_3$)$_2$<br>R$_9$ = H<br>R$_{10}$ = A | | |
| ClO$_4$<br>or<br>I | R$_6$ = Φ<br>R$_7$ = H<br>R$_8$ = A<br>R$_9$ = H<br>R$_{10}$ = Φ | | Φ-N(CH$_3$)$_2$ |
| ClO$_4$<br>or<br>I | R$_6$ = Φ<br>R$_7$ = H<br>R$_8$ = L-A<br>R$_9$ = H<br>R$_{10}$ = Φ | General Formula (II)<br>n = 0<br>Z = H | Φ-N(CH$_2$CH$_3$)$_2$ |
| ClO$_4$<br>or<br>I | R$_6$ = Φ<br>R$_7$ = H<br>R$_8$ = Φ<br>R$_9$ = H<br>R$_{10}$ = L-A | General Formula (II)<br>n = 0<br>Z = H | Φ-N(CH$_3$)$_2$ |
| ClO$_4$<br>or<br>I | R$_6$ = Φ<br>R$_7$ = H<br>R$_8$ = L-A<br>R$_9$ = H<br>R$_{10}$ = Φ | General Formula (II)<br>n = 1<br>Z = H | Φ-N(CH$_3$)$_2$ |
| ClO$_4$<br>or<br>I | R$_6$ = Φ<br>R$_7$ = H<br>R$_8$ = L-A<br>R$_9$ = H<br>R$_{10}$ = Φ | General Formula (II)<br>n = 1<br>Z =<br>(−)CH═CH-Φ-N(CH$_3$)$_2$ | Φ-N(CH$_3$)$_2$ |
| ClO$_4$<br>or<br>I | R$_6$ = Φ<br>R$_7$ = H<br>R$_8$ = L-A<br>R$_9$ = H<br>R$_{10}$ = Φ | General Formula (III)<br>n = 1 | Φ-N(CH$_3$)$_2$ |
| ClO$_4$<br>or<br>I | R$_6$ = Φ<br>R$_7$ = H<br>R$_8$ = L-A<br>R$_9$ = H<br>R$_{10}$ = Φ | General Formula (IV) | Φ-N(CH$_2$CH$_3$)$_2$ |
| ClO$_4$<br>or<br>I | R$_6$ = Φ<br>R$_7$ = H<br>R$_8$ = Φ<br>R$_9$ = H<br>R$_{10}$ = L-A | General Formula (IV) | Φ-N(CH$_2$CH$_3$)$_2$ |
| ClO$_4$<br>or<br>I | R$_6$ = Φ<br>R$_7$ = H<br>R$_8$ = Φ<br>R$_9$ = H<br>R$_{10}$ = L-A | General Formula (V) | 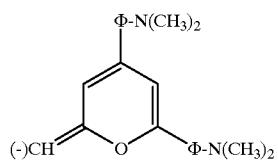 |
| ClO$_4$<br>or<br>I | R$_6$ = Φ<br>R$_7$ = H<br>R$_8$ = Φ<br>R$_9$ = H<br>R$_{10}$ = L-A | General Formula (V) | 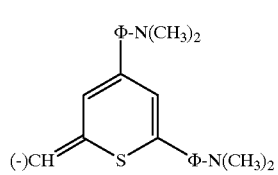 |

-continued

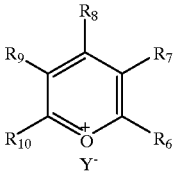

| Y | $R_i$ | L | A |
|---|---|---|---|
| $ClO_4$ or I | $R_6 = \Phi$<br>$R_7 = H$<br>$R_8 = \Phi$<br>$R_9 = H$<br>$R_{10} = L-A$ | General Formula (VI) | 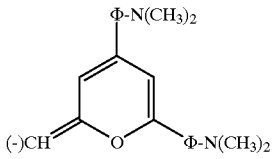 |
| $ClO_4$ or I | $R_6 = \Phi$<br>$R_7 = H$<br>$R_8 = \Phi$<br>$R_9 = H$<br>$R_{10} = L-A$ | General Formula (VI) | 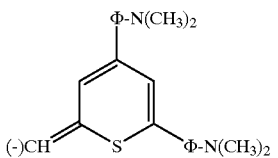 |
| $ClO_4$ or I | $R_6 = \Phi$<br>$R_7 = H$<br>$R_8 = \Phi$<br>$R_9 = H$<br>$R_{10} = L-A$ | General Formula (II)<br>$n = 0$<br>$Z = H$ | 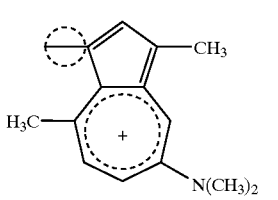 |
| $ClO_4$ or I | $R_6 = \Phi$<br>$R_7 = H$<br>$R_8 = \Phi$<br>$R_9 = H$<br>$R_{10} = L-A$ | General Formula (II)<br>$n = 0$<br>$Z = H$ | 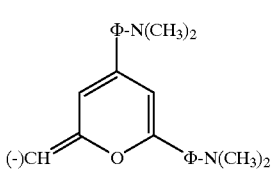 |
| $ClO_4$ or I | $R_6 = \Phi$<br>$R_7 = H$<br>$R_8 = \Phi$<br>$R_9 = H$<br>$R_{10} = L-A$ | General Formula (II)<br>$n = 0$<br>$Z = H$ | 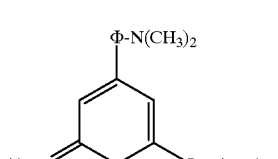 |
| $ClO_4$ or I | $R_6 = \Phi$<br>$R_7 = H$<br>$R_8 = L-A$<br>$R_9 = H$<br>$R_{10} = \Phi$ | General Formula (II)<br>$n = 0$<br>$Z = H$ | 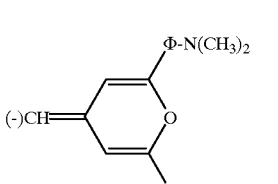 |
| $ClO_4$ or I | $R_6 = \Phi$<br>$R_7 = H$<br>$R_8 = L-A$<br>$R_9 = H$<br>$R_{10} = \Phi$ | General Formula (II)<br>$n = 0$<br>$Z = H$ | 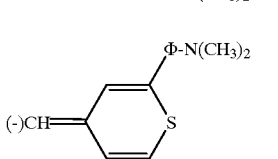 |
| $ClO_4$ or I | $R_6 = \Phi\text{-}N(CH_3)_2$<br>$R_7 = H$<br>$R_8 = A$ | | $\Phi\text{-}N(CH_3)_2$ |

-continued

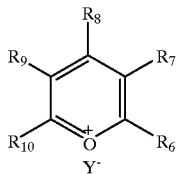

| Y | $R_i$ | L | A |
|---|---|---|---|
| ClO$_4$ or I | $R_9$ = H<br>$R_{10}$ = Φ-N(CH$_3$)$_2$<br>$R_6$ = Φ-N(CH$_3$)$_2$<br>$R_7$ = H<br>$R_8$ = A | | CH$_3$ |
| ClO$_4$ or I | $R_9$ = H<br>$R_{10}$ = Φ-N(CH$_3$)$_2$<br>$R_6$ = Φ-N(CH$_3$)$_2$<br>$R_7$ = H<br>$R_8$ = A | | Φ-COOH |
| ClO$_4$ or I | $R_9$ = H<br>$R_{10}$ = Φ-N(CH$_3$)$_2$<br>$R_6$ = Φ-N(CH$_3$)$_2$<br>$R_7$ = H<br>$R_8$ = L-A | General Formula (II)<br>n = 0<br>Z = H | Φ-N(CH$_3$)$_2$ |
| ClO$_4$ or I | $R_9$ = H<br>$R_{10}$ = Φ-N(CH$_3$)$_2$<br>$R_6$ = Φ-N(CH$_3$)$_2$<br>$R_7$ = H<br>$R_8$ = L-A | General Formula (II)<br>n = 1<br>Z = H | Φ-N(CH$_3$)$_2$ |
| ClO$_4$ or I | $R_9$ = H<br>$R_{10}$ = Φ-N(CH$_3$)$_2$<br>$R_6$ = Φ-N(CH$_3$)$_2$<br>$R_7$ = H<br>$R_8$ = L-A | General Formula (III)<br>n = 1 | Φ-N(CH$_3$)$_2$ |
| ClO$_4$ or I | $R_9$ = H<br>$R_{10}$ = Φ-N(CH$_3$)$_2$<br>$R_6$ = Φ-N(CH$_3$)$_2$<br>$R_7$ = H<br>$R_8$ = L-A | General Formula (IV) | Φ-N(CH$_3$)$_2$ |
| ClO$_4$ or I | $R_9$ = H<br>$R_{10}$ = Φ-N(CH$_3$)$_2$<br>$R_6$ = Φ-N(CH$_3$)$_2$<br>$R_7$ = H<br>$R_8$ = L-A | General Formula (II)<br>n = 0<br>Z = H | Φ-COOH |
| ClO$_4$ or I | $R_9$ = H<br>$R_{10}$ = Φ-N(CH$_3$)$_2$<br>$R_6$ = Φ-N(CH$_3$)$_2$<br>$R_7$ = H<br>$R_8$ = L-A | General Formula (II)<br>n = 1<br>Z = H | Φ-COOH |
| ClO$_4$ or I | $R_9$ = H<br>$R_{10}$ = Φ-N(CH$_3$)$_2$<br>$R_6$ = Φ-N(CH$_3$)$_2$<br>$R_7$ = H<br>$R_8$ = L-A | General Formula (III)<br>n = 1 | Φ-COOH |
| ClO$_4$ or I | $R_9$ = H<br>$R_{10}$ = Φ-N(CH$_3$)$_2$<br>$R_6$ = Φ-N(CH$_3$)$_2$<br>$R_7$ = H<br>$R_8$ = L-A | General Formula (IV) | Φ-COOH |
| ClO$_4$ or I | $R_9$ = H<br>$R_{10}$ = Φ-N(CH$_3$)$_2$<br>$R_6$ = L-A<br>$R_7$ = H<br>$R_8$ = Φ-N(CH$_3$)$_2$ | General Formula (II)<br>n = 0<br>Z = H | Φ-N(CH$_3$)$_2$ |
| ClO$_4$ or I | $R_9$ = H<br>$R_{10}$ = Φ-N(CH$_3$)$_2$<br>$R_6$ = L-A<br>$R_7$ = H<br>$R_8$ = Φ-N(CH$_3$)$_2$ | General Formula (II)<br>n = 1<br>Z = H | Φ-N(CH$_3$)$_2$ |
| ClO$_4$ or I | $R_9$ = H<br>$R_{10}$ = Φ-N(CH$_3$)$_2$<br>$R_6$ = L-A<br>$R_7$ = H<br>$R_8$ = Φ-N(CH$_3$)$_2$<br>$R_9$ = H<br>$R_{10}$ = Φ-N(CH$_3$)$_2$ | General Formula (III)<br>n = 1 | Φ-N(CH$_3$)$_2$ |

-continued

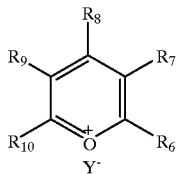

| Y | $R_i$ | L | A |
|---|---|---|---|
| $ClO_4$ or I | $R_6$ = L-A<br>$R_7$ = H<br>$R_8$ = Φ-N(CH$_3$)$_2$<br>$R_9$ = H<br>$R_{10}$ = Φ-N(CH$_3$)$_2$ | General Formula (IV) | Φ-N(CH$_3$)$_2$ |
| $ClO_4$ or I | $R_6$ = L-A<br>$R_7$ = H<br>$R_8$ = Φ-N(CH$_3$)$_2$<br>$R_9$ = H<br>$R_{10}$ = Φ-N(CH$_3$)$_2$ | General Formula (II)<br>n = 0<br>Z = H | Φ-COOH |
| $ClO_4$ or I | $R_6$ = L-A<br>$R_7$ = H<br>$R_8$ = Φ-N(CH$_3$)$_2$<br>$R_9$ = H<br>$R_{10}$ = Φ-N(CH$_3$)$_2$ | General Formula (II)<br>n = 1 | Φ-COOH |
| $ClO_4$ or I | $R_6$ = L-A<br>$R_7$ = H<br>$R_8$ = Φ-N(CH$_3$)$_2$<br>$R_9$ = H<br>$R_{10}$ = Φ-N(CH$_3$)$_2$ | General Formula (III)<br>n = 1 | Φ-COOH |
| $ClO_4$ or I | $R_6$ = L-A<br>$R_7$ = H<br>$R_8$ = Φ-N(CH$_3$)$_2$<br>$R_9$ = H<br>$R_{10}$ = Φ-N(CH$_3$)$_2$ | General Formula (IV) | —COOH |
| $ClO_4$ or I | $R_6$ = A<br>$R_7$ = H<br>$R_8$ = Φ-N(CH$_3$)$_2$<br>$R_9$ = H<br>$R_{10}$ = Φ-N(CH$_3$)$_2$ | | —COOH |
| $ClO_4$ or I | $R_6$ = A<br>$R_7$ = H<br>$R_8$ = Φ-N(CH$_3$)$_2$<br>$R_9$ = H<br>$R_{10}$ = Φ-N(CH$_3$)$_2$ | | -Φ-COOH |
| $ClO_4$ or I | $R_6$ = Φ<br>$R_7$ = H<br>$R_8$ = Φ-N(CH$_3$)$_2$<br>$R_9$ = H<br>$R_{10}$ = Φ-N(CH$_3$)$_2$ | | |
| $ClO_4$ or I | $R_6$ = Φ-N(CH$_3$)$_2$<br>$R_7$ = H<br>$R_8$ = Φ<br>$R_9$ = H<br>$R_{10}$ = Φ-N(CH$_3$)$_2$ | | | wherein the general formulae (II), (III), (IV), (V) and (VI) for L are:

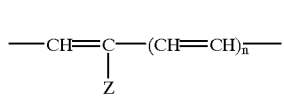 (II)

wherein Z is a hydrogen atom or a substituted or unsubstituted lower alkylene group, and n is 0, 1 or 2,

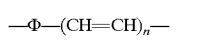 (III)

wherein n is 0, 1 or 2, and Φ is a substituted or unsubstituted o-, m- or p-phenylene group,

—CH=CH—Φ—CH=CH— (IV)

wherein Φ is a substituted or unsubstituted o-, m- or p-phenylene group,

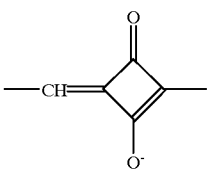 (V)

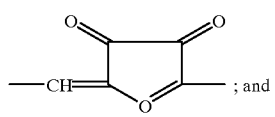 (VI)
(b) irradiating the cancer cells with light of at least a wavelength of 600 nm, the light being effectively absorbed by said compound for a period of time sufficient to induce death of the cancer cells.
* * * * *

UNITED STATES PATENT AND TRADEMARK OFFICE
CERTIFICATE OF CORRECTION

PATENT NO.   : 6,242,477 B1
DATED        : June 5, 2001
INVENTOR(S)  : Tadashi Okamoto et al.

It is certified that error appears in the above-identified patent and that said Letters Patent is hereby corrected as shown below:

Title page,
Item [56], References Cited, OTHER PUBLICATIONS,
After "Balaban, et al.," "3-Methyl ro 3-Phenyl Groups"," should read -- 3-Methyl or 3-Phenyl Groups", --; and after "Shimidzu, et al.," "iwth" should read -- with --; and
Item [57], ABSTRACT,
Line 8, "an" should read -- on --.

Column 2,
Line 33, "give" should read -- gives --; and
Line 44, "stronger However," should read -- stronger. However, --.

Column 3,
Line 48, "[IV];" (second occurrence) should read -- [VI]; --; and
Line 61, "f" should be deleted.

Column 4,
Line 36, "X" should read -- M --.

Column 5,
Line 11, "dimethylamono" should read -- dimethylamino --; and
Line 22, "containg" should read -- containing --.

Column 6,
Line 18, "ingredient" should read -- ingredients --.

Column 15,
Table 1, in: Compound No. 51, "General Formula [II]" should read -- General Formula [IV] --.

UNITED STATES PATENT AND TRADEMARK OFFICE
CERTIFICATE OF CORRECTION

PATENT NO.    : 6,242,477 B1
DATED         : June 5, 2001
INVENTOR(S)   : Tadashi Okamoto et al.

It is certified that error appears in the above-identified patent and that said Letters Patent is hereby corrected as shown below:

Column 17,
Line 60, "reaction, Afterward," should read -- reaction. Afterward, --; and
Line 63, "pottasium" should read -- potassium --.

Column 18,
Line 42, "IR (KBr) υV cm⁻¹:" should read -- IR (KBr) V cm$^{-1}$: --.

Column 21,
Line 20, "tht" should read -- that --.

Column 22,
Line 62, "-compounds" should read -- compounds --.

Column 25,
Line 55, "This" should read -- 40 This --.

Column 26,
Line 14, "This" should read -- 41 This --.

Column 34,
Line 9, "EXAMPLE6" should read -- EXAMPLE 6 --.

Column 35,
Table 6, "Inocculation" should read -- Inoculation --; and
Table 7, after "C'1", "6 × 6 × 3" should read -- 6 × 5 × 3 --.

Column 36,
Line 51, "inocculated" should read -- inoculated --.

UNITED STATES PATENT AND TRADEMARK OFFICE
CERTIFICATE OF CORRECTION

PATENT NO. : 6,242,477 B1
DATED : June 5, 2001
INVENTOR(S) : Tadashi Okamoto et al.

It is certified that error appears in the above-identified patent and that said Letters Patent is hereby corrected as shown below:

Column 45,
Table, "General Formula (II)
    n=1" should read -- General Formula (II)
        n=1
        Z=H --; and
Table, "General Formula (IV) —COOH" should read
    -- General Formula (IV) Φ-COOH --.

Signed and Sealed this

Ninth Day of April, 2002

Attest:

Attesting Officer

JAMES E. ROGAN
*Director of the United States Patent and Trademark Office*